(12) United States Patent
Gorin et al.

(10) Patent No.: US 12,399,187 B2
(45) Date of Patent: Aug. 26, 2025

(54) CONTROLLED BLOOD DELIVERY TO MIXING CHAMBER OF A BLOOD TESTING CARTRIDGE

(71) Applicant: CA CASYSO GMBH, Basel (CH)

(72) Inventors: Michael M. Gorin, Incline Village, NV (US); Robert S. Hillman, San Diego, CA (US); Cory Lee McCluskey, Encinitas, CA (US); Hubert Martin Schwaiger, Munich (DE)

(73) Assignee: CA Casyso GMBH, Basel (CH)

( * ) Notice: Subject to any disclaimer, the term of this patent is extended or adjusted under 35 U.S.C. 154(b) by 142 days.

(21) Appl. No.: 16/572,567

(22) Filed: Sep. 16, 2019

(65) Prior Publication Data

US 2020/0011884 A1  Jan. 9, 2020

(51) Int. Cl.
*G01N 33/86* (2006.01)
*B01F 33/452* (2022.01)
(Continued)

(52) U.S. Cl.
CPC ........... *G01N 33/86* (2013.01); *B01F 33/452* (2022.01); *B01F 33/813* (2022.01);
(Continued)

(58) Field of Classification Search
CPC .... G01N 33/4905; G01N 33/86; G01N 11/00; G01N 11/14; G01N 1/38; G01N 35/1079;
(Continued)

(56) References Cited

U.S. PATENT DOCUMENTS

| 2,555,937 A | 6/1951 | Rosenthal et al. |
| 2,995,425 A | 8/1961 | Fuhrmann |

(Continued)

FOREIGN PATENT DOCUMENTS

| CN | 1853104 | 10/2006 |
| CN | 1985168 A | 6/2007 |

(Continued)

OTHER PUBLICATIONS

Japan Patent Office, Notification of Reasons for Refusal, JP Patent Application No. 2019-001775, Jan. 31, 2020, 13 pages.
(Continued)

*Primary Examiner* — Dean Kwak
(74) *Attorney, Agent, or Firm* — ArentFox Schiff LLP

(57) ABSTRACT

Embodiments of a blood coagulation testing system can operate as an automated thromboelastometry system that is particularly useful, for example, at a point-of-care site. In some embodiments, the blood coagulation testing system includes a single-use cartridge component configured to measure and mix reagents with blood received from a blood sample reservoir. A mixing chamber in the single-use cartridge includes different reagent beads that, when exposed to a pre-determined volume of blood, dissolve and mix specific reagents with the blood. The assembled blood cartridge further includes configurations that are designed to prevent blood from prematurely mixing with reagent beads in the mixing chamber and to guide blood flow in the mixing chamber to dissolve reagent beads in a desired order. Thus, the mixture obtained from the mixing chamber can be readily utilized to generate results for the blood coagulation testing system.

20 Claims, 11 Drawing Sheets

(51) Int. Cl.
  *B01F 33/81* (2022.01)
  *B01L 3/00* (2006.01)
  *G01N 1/38* (2006.01)
  *G01N 35/04* (2006.01)
  *G01N 35/10* (2006.01)

(52) U.S. Cl.
  CPC .......... *B01L 3/502746* (2013.01); *G01N 1/38* (2013.01); *B01L 2200/0621* (2013.01); *B01L 2200/0668* (2013.01); *B01L 2400/086* (2013.01); *G01N 2035/0436* (2013.01); *G01N 35/1079* (2013.01); *G01N 35/1097* (2013.01)

(58) Field of Classification Search
  CPC ........ G01N 35/1097; G01N 2035/0436; B01F 13/0059; B01F 13/0818; B01F 13/1022; B01F 15/04; B01L 3/502746; B01L 2200/0668; B01L 2400/086; B01L 2200/0621; B01L 2200/0684; B01L 2200/10; B01L 2300/0627; B01L 2300/087; B01L 2400/049; B01L 2400/0694; B01L 3/502; B01L 3/5027; B01L 3/561; B01L 3/567
  USPC ....... 422/400, 401, 408, 417, 500, 547, 554, 422/546, 559, 560, 561, 430, 73; 436/10; 435/287.1
  See application file for complete search history.

(56) References Cited

U.S. PATENT DOCUMENTS

| | | | |
|---|---|---|---|
| 3,714,815 A | 2/1973 | Hartert | |
| 3,803,903 A | 4/1974 | Lin | |
| 3,903,903 A | 9/1975 | Matsumura | |
| 4,148,216 A | 4/1979 | Do et al. | |
| 4,193,293 A | 3/1980 | Cavallari | |
| D260,428 S | 8/1981 | Fekete | |
| 4,319,194 A | 3/1982 | Cardinal et al. | |
| 4,599,219 A | 7/1986 | Cooper et al. | |
| 4,726,220 A | 2/1988 | Feier et al. | |
| 4,752,449 A | 6/1988 | Jackson et al. | |
| 4,753,776 A | 6/1988 | Hillman et al. | |
| 4,756,884 A | 7/1988 | Hillman et al. | |
| 4,765,180 A | 8/1988 | Clifton | |
| 4,767,600 A | 8/1988 | Vicario | |
| D302,294 S | 7/1989 | Hillman | |
| 4,868,129 A | 9/1989 | Gibbons et al. | |
| D305,360 S | 1/1990 | Fechtner | |
| 4,948,961 A | 8/1990 | Hillman et al. | |
| 4,956,089 A | 9/1990 | Hurst | |
| 4,963,498 A | 10/1990 | Hillman et al. | |
| 5,009,316 A | 4/1991 | Klein | |
| 5,028,142 A | 7/1991 | Ostoich et al. | |
| 5,077,017 A | 12/1991 | Gorin et al. | |
| 5,104,813 A | 4/1992 | Besemer et al. | |
| D327,743 S | 7/1992 | Frenkel et al. | |
| 5,162,237 A | 11/1992 | Messenger et al. | |
| 5,164,598 A | 11/1992 | Hillman et al. | |
| 5,207,988 A | 5/1993 | Lucas | |
| 5,222,808 A | 6/1993 | Sugarman et al. | |
| 5,223,219 A | 6/1993 | Subramanian et al. | |
| 5,223,227 A | 6/1993 | Zuckerman | |
| 5,287,732 A | 2/1994 | Sekiguchi | |
| D347,067 S | 5/1994 | Shartle et al. | |
| 5,447,440 A | 9/1995 | Davis et al. | |
| 5,531,102 A | 7/1996 | Brookfield et al. | |
| 5,777,212 A | 7/1998 | Sekiguchi et al. | |
| 5,777,215 A | 7/1998 | Calatzis et al. | |
| 5,788,928 A | 8/1998 | Carey et al. | |
| 5,902,937 A | 5/1999 | Amrani et al. | |
| 6,012,712 A | 1/2000 | Bernstein | |
| 6,066,243 A | 5/2000 | Anderson et al. | |
| 6,200,532 B1 | 3/2001 | Wu et al. | |
| 6,448,024 B1 | 9/2002 | Bruegger | |
| 6,537,819 B2 | 3/2003 | Cohen et al. | |
| 6,613,286 B2 | 9/2003 | Braun et al. | |
| D481,133 S | 10/2003 | Blouin et al. | |
| D482,454 S | 11/2003 | Gebrian | |
| 6,662,031 B1 | 12/2003 | Khalil et al. | |
| 6,699,718 B1 | 3/2004 | Bruegger | |
| 6,750,053 B1 | 6/2004 | Widrig Opalsky et al. | |
| 6,838,055 B2 | 1/2005 | Sando et al. | |
| 6,942,836 B2 | 9/2005 | Freudenthal et al. | |
| 6,951,127 B1 | 10/2005 | Bi | |
| 6,979,569 B1 | 12/2005 | Carver et al. | |
| 7,399,637 B2 | 7/2008 | Wright et al. | |
| 7,412,877 B1 | 8/2008 | Bi | |
| 7,422,905 B2 | 9/2008 | Clague et al. | |
| 7,491,175 B2 | 2/2009 | Ruether et al. | |
| 7,497,997 B2 | 3/2009 | Glezer et al. | |
| 7,524,670 B2 | 4/2009 | Cohen et al. | |
| 7,595,169 B2 | 9/2009 | Swaim et al. | |
| 7,732,213 B2 | 6/2010 | Cohen et al. | |
| 7,745,223 B2 | 6/2010 | Schubert et al. | |
| 7,811,792 B2 | 10/2010 | Cohen et al. | |
| 7,901,629 B2 | 3/2011 | Calatzis et al. | |
| 7,947,505 B2 | 5/2011 | Kawasaki et al. | |
| 7,951,606 B2 | 5/2011 | Pei et al. | |
| 8,003,401 B2 | 8/2011 | Tonnessen et al. | |
| D645,973 S | 9/2011 | Hoenes | |
| 8,110,392 B2 | 2/2012 | Battrell et al. | |
| 8,168,442 B2 | 5/2012 | Petersen et al. | |
| 8,383,045 B2 | 2/2013 | Schubert et al. | |
| 8,448,499 B2 | 5/2013 | Schubert et al. | |
| 8,857,244 B2 | 10/2014 | Schubert et al. | |
| 9,061,280 B2 | 6/2015 | Tanaami et al. | |
| D737,993 S | 9/2015 | Tan et al. | |
| 9,272,280 B2 | 3/2016 | Viola et al. | |
| 9,285,377 B2 | 3/2016 | Schubert et al. | |
| D777,343 S | 1/2017 | Gorin et al. | |
| 2002/0081741 A1 | 6/2002 | Braun et al. | |
| 2002/0177958 A1 | 11/2002 | Widrig Opalsky et al. | |
| 2003/0073244 A1 | 4/2003 | Cohen et al. | |
| 2004/0072278 A1 | 4/2004 | Chou et al. | |
| 2004/0089616 A1 | 5/2004 | Kellogg et al. | |
| 2004/0131500 A1 | 7/2004 | Chow | |
| 2005/0136541 A1 | 6/2005 | De Haan | |
| 2005/0233460 A1 | 10/2005 | Clague et al. | |
| 2005/0233466 A1 | 10/2005 | Wright et al. | |
| 2007/0059208 A1* | 3/2007 | Desmond .............. | B01L 3/5025 422/400 |
| 2007/0059840 A1 | 3/2007 | Cohen et al. | |
| 2007/0099290 A1 | 5/2007 | Iida et al. | |
| 2007/0140902 A1 | 6/2007 | Calatzis et al. | |
| 2007/0243105 A1 | 10/2007 | Kratzer et al. | |
| 2008/0026476 A1 | 1/2008 | Howell et al. | |
| 2008/0160500 A1 | 7/2008 | Fuller et al. | |
| 2008/0194041 A1 | 8/2008 | Guirguis | |
| 2008/0227217 A1 | 9/2008 | Yamamoto et al. | |
| 2008/0251383 A1 | 10/2008 | Sobek et al. | |
| 2008/0261261 A1 | 10/2008 | Grimes et al. | |
| 2008/0297169 A1 | 12/2008 | Greenquist et al. | |
| 2009/0130645 A1 | 5/2009 | Schubert et al. | |
| 2009/0181411 A1 | 7/2009 | Battrell et al. | |
| 2010/0056383 A1* | 3/2010 | Ririe .............. | G01N 33/54386 506/7 |
| 2010/0154520 A1 | 6/2010 | Schubert et al. | |
| 2010/0184201 A1 | 7/2010 | Schubert et al. | |
| 2011/0201099 A1 | 8/2011 | Anderson et al. | |
| 2011/0237913 A1 | 9/2011 | Schubert et al. | |
| 2011/0252352 A1 | 10/2011 | Viola et al. | |
| 2012/0084022 A1 | 4/2012 | Giovangrandi et al. | |
| 2012/0294767 A1 | 11/2012 | Viola et al. | |
| 2012/0329082 A1 | 12/2012 | Viola et al. | |
| 2013/0137172 A1 | 5/2013 | Ririe et al. | |
| 2013/0270113 A1 | 10/2013 | Huang | |
| 2013/0323846 A1 | 12/2013 | Schubert et al. | |
| 2013/0323847 A1 | 12/2013 | Schubert et al. | |
| 2013/0323848 A1 | 12/2013 | Schubert et al. | |
| 2013/0333448 A1 | 12/2013 | Schubert et al. | |
| 2014/0004613 A1 | 1/2014 | Goldstein | |
| 2014/0271409 A1 | 9/2014 | Knight et al. | |

(56) References Cited

U.S. PATENT DOCUMENTS

| | | |
|---|---|---|
| 2014/0328732 A1 | 11/2014 | Delmenico et al. |
| 2015/0253271 A1 | 9/2015 | Giridhar et al. |
| 2015/0316460 A1* | 11/2015 | Redl .................. G01N 33/86 435/13 |
| 2016/0091483 A1 | 3/2016 | McCluskey et al. |
| 2016/0091509 A1 | 3/2016 | Di Tullio et al. |
| 2016/0091511 A1 | 3/2016 | Di Tullio et al. |
| 2016/0091514 A1 | 3/2016 | Gorin et al. |
| 2016/0091515 A1 | 3/2016 | Gorin et al. |
| 2016/0091516 A1 | 3/2016 | Gorin et al. |
| 2016/0091517 A1 | 3/2016 | Gorin et al. |
| 2016/0195557 A1 | 7/2016 | Schubert et al. |
| 2016/0313357 A1 | 10/2016 | Viola et al. |
| 2016/0361715 A1 | 12/2016 | Shi et al. |
| 2016/0377638 A1 | 12/2016 | Bels et al. |
| 2017/0254318 A1 | 9/2017 | Lee et al. |
| 2018/0133714 A1 | 5/2018 | Wo et al. |

FOREIGN PATENT DOCUMENTS

| | | |
|---|---|---|
| CN | 101195112 A | 6/2008 |
| CN | 101301632 A | 11/2008 |
| CN | 101563562 A | 10/2009 |
| CN | 102265151 A | 11/2011 |
| CN | 103170377 A | 6/2013 |
| CN | 103175950 A | 6/2013 |
| CN | 103217401 A | 7/2013 |
| CN | 104204787 A | 12/2014 |
| CN | 104903728 A | 9/2015 |
| DE | 2740932 A1 | 11/1978 |
| DE | 10135569 A1 | 2/2003 |
| DE | 202014002289 | 9/2014 |
| EP | 0404456 A2 | 12/1990 |
| EP | 1367392 A1 | 12/2003 |
| EP | 1394546 A1 | 3/2004 |
| EP | 1627725 A2 | 2/2006 |
| EP | 1884778 A1 | 2/2008 |
| EP | 1901065 | 3/2008 |
| EP | 2208996 | 9/2010 |
| EP | 2202517 | 8/2012 |
| EP | 3001196 A2 | 3/2016 |
| GB | 2257256 A | 1/1993 |
| JP | 1971-004947 | 11/1971 |
| JP | 1987-140047 | 6/1987 |
| JP | 1991-031764 | 2/1991 |
| JP | H05-149958 A | 6/1993 |
| JP | 1997-159596 | 6/1997 |
| JP | 09-507580 A | 7/1997 |
| JP | 2001-516880 A | 10/2001 |
| JP | 2005-149958 A | 6/2005 |
| JP | 2005-518531 A | 6/2005 |
| JP | 2005-534895 A | 11/2005 |
| JP | 2006-053142 A | 2/2006 |
| JP | 2007-532878 A | 11/2007 |
| JP | 2008-534972 A | 8/2008 |
| JP | 2008/302322 | 12/2008 |
| JP | 2009-506332 A | 2/2009 |
| JP | 2009-121912 A | 6/2009 |
| JP | 2009-229324 A | 10/2009 |
| JP | 2010-078575 A | 4/2010 |
| JP | 2010-266453 A | 11/2010 |
| JP | 2011-174952 A | 9/2011 |
| JP | 2012-513582 A | 6/2012 |
| JP | 2012-515340 | 7/2012 |
| JP | 2013-524176 A | 6/2013 |
| JP | 2014-010109 A | 1/2014 |
| JP | 2015-045642 | 3/2015 |
| JP | 2016-118530 A | 6/2016 |
| WO | WO 1989/006803 A1 | 7/1989 |
| WO | WO 96/38730 A1 | 12/1996 |
| WO | WO 2002/050535 | 6/2002 |
| WO | WO 2002/063273 A2 | 8/2002 |
| WO | WO 2005/106467 A1 | 11/2005 |
| WO | WO 2006/091650 A2 | 8/2006 |
| WO | WO 2006/126290 A1 | 11/2006 |
| WO | WO 2007/047961 A2 | 4/2007 |
| WO | WO 2008/075181 | 6/2008 |
| WO | WO-2006/137334 | 1/2009 |
| WO | WO 2009/073851 A1 | 6/2009 |
| WO | WO 2010/072620 A1 | 7/2010 |
| WO | WO 2008/093216 A1 | 8/2011 |
| WO | WO 2011/117017 A1 | 9/2011 |
| WO | WO 2013/172003 A1 | 11/2013 |
| WO | WO 2014/103744 | 7/2014 |
| WO | WO 2014/115478 | 7/2014 |
| WO | WO 2014/162285 A1 | 10/2014 |
| WO | WO 2014/172243 A1 | 10/2014 |
| WO | WO 2016/196236 | 12/2016 |
| WO | WO 2017/096284 A1 | 6/2017 |

OTHER PUBLICATIONS

China National Intellectual Property Administration, Office Action, CN Patent Application No. 201880056029.8, Sep. 15, 2020, 12 pages (with concise explanation of relevance).

Japan Patent Office, Official Notice of Rejection, JP Patent Application No. 2020-501278, Jul. 14, 2020, eight pages.

"HealthPACT," "Rotational thromboelastometry (ROTEM)-targeted therapy for coagulation management in patitnets with massive bleeding," "Health Policy Advisory Committee on Technology. Retrieved from the Internet: < URL:https://www.heath.qld.gov.au/healthpact/docs/briefs/WP024.pdg>-, 30 pages, Nov. 2012".

Anonymous: Rotem delta Whole Blood Haemostasis System using Thromboelastometry US Operating Manual,: [retrieved on Oct. 30, 2015]. Retrieved from the internet: < URL: http://www.sfgh-poct.org/wp-content/uploads/2013/02/ROTEM-delta-US-Operat- ing-Manual-Part-12.pdf>, Sep. 2012.

Calatzis et al., "Strategies to Assess Individual Susceptibility to abciximab Therapy Using a New Functional Assay," Annals of Hematology, (Berlin, DE) vol. 76, No. Suppl 1, p. A61, XP009097526, 1998.

Chakroun et al., "The influence of fibrin polymerization and platelet-mediated contractile forces on citrated whole blood thromboelastography profile," Thromb Haemost., 95(5):822-828, May 2006.

Chinese Office Action (OA) for App. No. 200980151858.5 dated May 21, 2013, 16 pgs.

Chinese Office Action for App. No. 200980151858.5 dated Feb. 14, 2014, 4 pgs.

European Extended search report for App No. 13167983.9, dated Nov. 6, 2013, 3 pgs.

European Office Action for App. No. 08172769.5, dated Jun. 1, 2011, 12 pgs.

European Office Action for App. No. 12179576.9, dated May 22, 2013, 10 pgs.

European Office Action for App. No. 13167979.7, dated Nov. 15, 2016, 8pgs.

European Office Action for Application No. 13163014.7, dated Mar. 24, 2014, 12 pages.

European Search Report and Opinion for Application No. 15187347.8, dated Jun. 1, 2016 (16 Pages).

First Office Action with concise explanation of relevance, Chinese Patent Application No. 201680074338.9, dated Feb. 3, 2019, 5 pages.

Greilich et al., "Near-site monitoring of the antiplatelet drug abciximab using the Hemodyne analyzer and modified thrombelastograph," J Cardiothorac Vase Anesth., 13(1):58-64, Feb. 1999.

Hartert, "Blood Coagulation Studies with Thromboelastography—A New Research Method," Klin Wochenschrift 26:577-583, Oct. 1948 [English translation].

International Preliminary report on patentability for PCT/EP2009/067181, dated Jun. 29, 2011, 9 pgs.

International search report and written opinion for Ap. No. PCT/EP2009/067181, dated Mar. 22, 2010, 12 pgs.

Japan Patent Office, Office Action, Japanese Patent Application No. 2018-528982, dated Jul. 2, 2019, 14 pages.

Japanese Notification for Refusal for Application No. 2011-541392, dated Jun. 14, 2013, 4 pages.

(56) References Cited

OTHER PUBLICATIONS

Japanese notification of refusal for Ap. No. 2014-165975, dated Jul. 17, 2015, 8 pgs.
Japanese Office Action, Japanese Application No. 2015-191180, dated Nov. 17, 2017, 9 pages.
Kawasaki et al., "The effects of vasoactive agents, platelet agonists and anticoagulation on thrombelastography," ActaAnaesthesiol Scand., 51(9):1237-1244, Oct. 2007.
Khurana et al., "Monitoring platelet glycoprotein lib/llia-fibrin interaction with tissue factor-activated thromboelastography," J Lab Clin Med., 130(4):401-411, Oct. 1997.
Korean Office Action for Ap. No. 1020117017187, dated Mar. 28, 2016, 11 pgs.
Korean Office Action for Application No. 1020167029191, dated Nov. 17, 2016, 5 pgs.
Lang et al., "Evaluation of the new device ROTEM platelet" [retrieved on Oct. 28, 2015]. Retrieved from the Internet: <URL: https://www.rotem.de/wp-content/uploads/2014-09-Lang-et-al-2014.pdf>, Jan. 1, 2014.
National Intellectual Property Administration of China, Office Action, Chinese Patent Application No. 2016800743389,, 7 pages.
Nield et al., "MRI-based blood oxygen saturation measurements in infants and children with congenital heart disease," Pediatr Radiol., 32(7):518-522. Epub Apr. 16, 2002.
Nielsen et al., "Evaluation of the contribution of platelets to clot strength by thromboelastography in rabbits: the role of tissue factor and cytochalasin D," Anesth Anafa., 91(1):35-39, Jul. 2000.
Noon et al., "Reduction of blood trauma in roller pumps for long-term perfusion" World J Surg., 9(1):65-71, Feb. 1985.
Notification of reasons for refusal for Ap. No. 2015-132034, dated Jul. 29, 2016, 5 pgs.
Novotny et al., "Platelets secrete a coagulation inhibitor functionally and antigenically similar to the lipoprotein associated coagulation inhibitor," Blood, 72(6):2020-2025, Dec. 1988.
Partial European search report, European Patent Application No. 18193752.5, dated Feb. 12, 2019, 15 pages.
PCT International Search Report and Written Opinion, PCT Application No. PCT/US16/34501, dated Aug. 31, 2016, 17 pages.
PCT International Search Report and Written Opinion, PCT Application No. PCT/US16/64800, dated Feb. 16, 2017, 14 pages.
PCT International Search Report and Written Opinion, PCT Application No. PCT/US18/40120, dated Sep. 20, 2018, 13 pages.
PCT International Search Report and Written Opinion, PCT Application No. PCT/US2016/064790, dated Feb. 15, 2017, 17 pages.
PCT International Search Report and Written Opinion, PCT Application No. PCT/US2016/064797, dated Feb. 15, 2017, 16 pages.
PCT International Search Report and Written Opinion, PCT Application No. PCT/US2016/064806, dated Feb. 15, 2017, 18 pages.
PCT International Search Report and Written Opinion, PCT Application No. PCT/US2017/049505, dated Nov. 2, 2017, 17 pages.
Prisco and Paniccia, "Point-of-Care Testing ofHemostasis in Cardiac Surgery", Thromb J., 1(1):1, May 6, 2003.
Rodzynek et al., "The transfer test: a new screening procedure for thrombotic diseases," J Surg Res., 35(3):227-233, Sep. 1983.
ROTEM.RTM. "Targeted therapy for coagulation management in patients with massive bleeding," https://www.heath.qld.gov.au/_data/assets/pdf_file/0023/427145/wp024.pdf, Nov. 2012, 30 pgs, [brochure].
Rotem.RTM. "When Minutes Count to Stop the Bleeding," Pentapharm GmbH, www.rotem.de, 6 pages, Jun. 2007. [brochure].
ROTEM.RTM. delta, "Targeted therapy stops the bleeding," 6 pages, Jan. 6, 2014, [brochure].
ROTEM.RTM. delta, "Whole Blood Haemostasis System using Thromboelastomerty Operating Manual," 164 pages, Nov. 17, 2014 [brochure].
Rugeri et al., "Diagnosis of early coagulation abnormalities in trauma patients by rotation thrombelastography," J Thromb Haemost., 5(2):289-295, Epub Nov. 16, 2006.
Salooia and Perrv, "Thrombelastography," Blood Coa1ml Fibrinolysis, 12(5):327-37, Jul. 2001.
Shore-Lesserson et al., "Thromboelastography-guided transfusion algorithm reduces transfusions in complex cardiac surgery," Anesth Analg., 88(2):312-319, Feb. 1999.
Soria et al., "Fibrin stabilizing factor (F XIII) and collagen polymerization," Experientia, 31(11):1355-1357, Nov. 15, 1975.
Spannagl et al., "Point-of-Care Analysis of the Homostatic System," Laboratoriumsmedizin, (Kirchheim, DE), 26(1-2):68-76, Feb. 2002.
Srinivasa et al., "Thromboelastography: Where Is It and Where Is It Heading?" Int'l Anesthesiology Clinics, 39(1 ):35-49, Winter 2001.
Tanaka et al., "Thrombin generation assay and viscoelastic coagulation monitors demonstrate differences in the mode of thrombin inhibition between unfractionated heparin and bivalirudin," Anesth Analg., 105(4):933-939, Oct. 2007.
European Patent Office, Extended European Search Report and Opinion, European Patent Application No. 16871654.6, May 27, 2019, 7 pages.
Extended European Search Report for European Patent Application No. EP 18193752.5, dated May 13, 2019, 13 Pages.
United States Office Action, U.S. Appl. No. 14/958,889, filed Sep. 13, 2019, 18 pages.
United States Office Action, U.S. Appl. No. 15/648,345, filed Jan. 22, 2020, nine pages.
European Patent Office, Extended European Search Report, EP Patent Application No. 17847520.8, Feb. 27, 2020, seven pages.
Canadian Intellectual Property Office, Examiner Requisition, CA Patent Application No. 3,033,000, Apr. 15, 2020, four pages.
China National Intellectual Property Administration, Office Action, CN Patent Application No. 201880056029.8, Mar. 22, 2021, 13 pages.
European Patent Office, European Extended Search Report and Opinion, EP Patent Application No. 18831324.1, Mar. 17, 2021, eight pages.
Notice of Reason for Rejection for Japanese Patent Application No. 2019-508198, issued Nov. 18, 2020, (with English translation), 10 pages.
Decision of Rejection for Japanese Patent Application No. 2019-508198, issued Apr. 16, 2021, (with English translation), 11 pages.
Decision to Grant for Japanese Patent Application No. 2019-508198, issued Oct. 3, 2021, 3 pages.
Australian Examination Report No. 1 dated Aug. 21, 2021, Application No. 2017318576 (3 pgs.).

\* cited by examiner

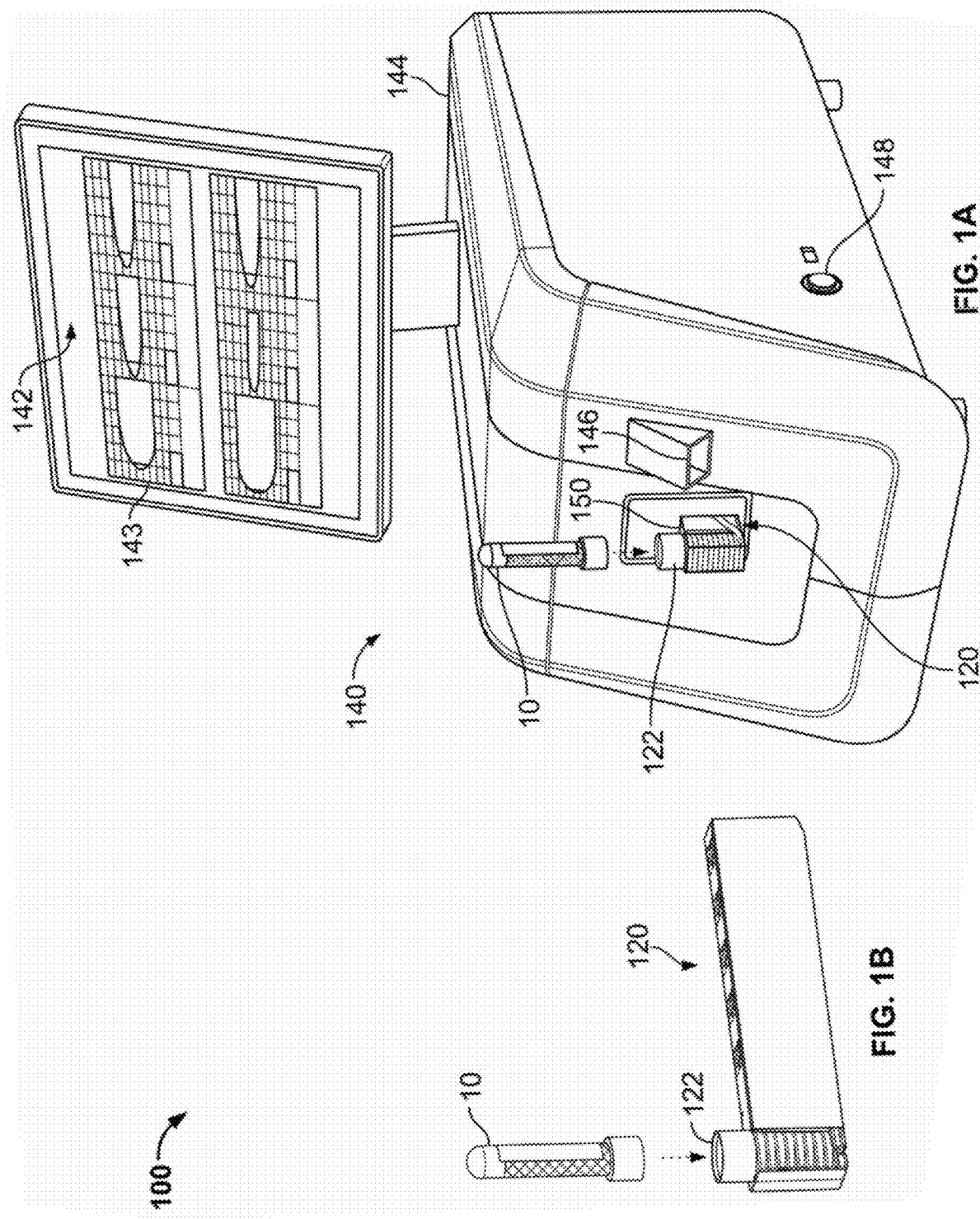

Section B-B

CONTROLLED BLOOD DELIVERY TO MIXING CHAMBER OF A BLOOD TESTING CARTRIDGE

CROSS REFERENCE TO RELATED APPLICATIONS

This application is a divisional of co-pending U.S. application Ser. No. 15/253,121, filed Aug. 31, 2016, which is incorporated by reference in its entirety.

TECHNICAL FIELD

This document relates to systems and methods for testing characteristics of a blood sample, more specifically to the controlled mixing of reagents with blood in a blood cartridge device for blood coagulation analysis.

BACKGROUND

Hemostasis is the human body's response to blood vessel injury and bleeding. Hemostasis involves a coordinated effort between platelets and numerous blood clotting proteins (or clotting factors), resulting in the formation of a blood clot and the subsequent stoppage of bleeding.

Various methods have been introduced to assess the potential of blood to form an adequate clot and to determine the blood clot's stability. Common laboratory tests such as thrombocyte counts or the determination of fibrin concentration provide information on whether the tested component is available in sufficient amount, but some of those tests might not answer the question of whether the tested component works properly under physiological conditions. Other laboratory tests work on blood plasma, which may impose additional preparation steps and additional time beyond what is preferred, for example, in the point-of-care context (e.g., in a surgical theater during a surgical operation).

Another group of tests to assess the potential of blood to form an adequate clot is known as "viscoelastic methods." In at least some viscoelastic methods, the blood clot firmness (or other parameters dependent thereon) is determined over a period of time, for example, from the formation of the first fibrin fibers until the dissolution of the blood clot by fibrinolysis. Blood clot firmness is a functional parameter which contributes to hemostasis in vivo, as a clot must resist blood pressure and shear stress at the site of vascular injury or incision. In many cases, clot firmness may result from multiple interlinked processes including coagulation activation, thrombin formation, fibrin formation and polymerization, platelet activation, and fibrin-platelet interaction.

To isolate and test particular functions of thrombocytes, fibrinogen, and other factors in a blood sample, reagent compounds can be mixed with the blood sample to activate or inhibit certain components in the blood sample. In some commercially available point-of-care blood testing systems, reagents are injected into a disposable plastic cup containing a blood sample, and the cup is then engaged by the control console of the blood testing system to evaluate characteristics of the coagulation/clotting of the blood sample.

Assorted assays require specific reagents that must be added according to a strict timed schedule or based on a particular order. A manual operator can achieve this by using pipettes for the dispensing and measuring of the reagents, blood, and mixed samples. However, this task is manually intensive. Many automated systems for testing blood have been implemented but they experience problems of blood leakage that prematurely adds reagents to the blood or fails to provide the appropriate reagents to the blood in the correct order.

SUMMARY

Some embodiments of a system for testing characteristics of a blood sample (which, as used herein, should be understood to include blood or derivatives of blood such as plasma) can include a cartridge configured to mate with a control console and receive a blood sample for a point-of-care whole blood coagulation analysis. In particular circumstances, the cartridge is configured to interact with the control console so as to perform a number of automated transport and testing operations on portions of the blood sample so as to provide reliable and prompt results indicative of a patient's blood characteristics at the point-of-care (e.g., while the patient is in a surgical room undergoing surgery). For example, the system can serve as an automated thromboelastometry system for providing detailed and prompt results of blood coagulation characteristics in response to receiving a cartridge (and blood sample at the cartridge) and an indication from an operator to begin the automated testing process.

In some embodiments, the thromboelastometry system includes a reusable analyzer console and one or more single-use cartridge components configured to mate with the console. In one example, to operate the thromboelastometry system, a user inserts the cartridge into the analyzer console and, when prompted by the analyzer console, inserts a blood collection tube (containing a whole blood sample) into a receiver portion of the cartridge. The user is then prompted a user interface of the analyzer console to initiate a number of automated blood transfer and testing operations. Thereafter, the analyzer console automatically performs (without requiring further user interaction with the cartridge or the blood sample) the testing and displays the results on a graphical display using qualitative graphical representations and quantitative parameters. In this particular example, no manual pipetting, mixing, or handling of reagents by the user is needed. In some embodiments, four or more assays are automatically performed on the blood sample using a single cartridge device. Such assays provide information on the whole kinetics of hemostasis, such as clotting time, clot formation, clot stability, and lysis; moreover, such information can be promptly output from a user interface of the system to provide reliable and prompt results indicative of a patient's blood characteristics at the point-of-care (e.g., while the patient is in a surgical room undergoing surgery).

Various embodiments described herein include a blood cartridge that may include a blood sample receiver and at least one blood sample pathway in selective fluid communication with the blood sample receiver. The blood sample pathway may include: a blood measurement chamber configured to be filled with a predetermined amount of a blood sample via the blood sample receiver, a reagent mixing chamber for receiving the predetermined amount of the blood sample from the blood measurement chamber and for mixing the predetermined amount of the blood sample with one or more reagents, and a blood coagulation blood testing chamber for receiving from the reagent mixing chamber the blood sample with one or more reagents mixed therewith, and an overflow chamber in fluid communication with the blood sample pathway so as to collect excess blood from the blood measurement chamber beyond the predetermined amount the blood sample.

In various embodiments described herein, a blood cartridge device for a measuring system for measuring characteristics of a blood sample may include a plurality of reagent mixing chambers for receiving and mixing a predetermined amount of a blood sample with one or more reagent beads. Each reagent mixing chamber may include configurations to prevent leaked blood from prematurely interacting with the one or more reagent beads. Additionally, each reagent mixing chamber may include configurations that direct the flow of a blood sample within the mixing chamber to preferentially dissolve a first type of reagent bead before a second type. The cartridge device may also include a plurality of retaining elements extending into the reagent mixing chamber so as to maintain a predetermined vertical position of each of the reagent mixing beads within the mixing chamber. The retaining elements of at least one of the reagent mixing chambers may engage multiple reagent mixing beads to maintain the multiple reagent mixing beads spaced apart from one another.

In particular embodiments described herein, the cartridge device may also include a movable mixing element retained with the reagent mixing chamber. The movable mixing element may comprise a material that is inert relative to the blood sample. The cartridge device may further include a plurality of retaining elements extending into the reagent mixing chamber so as to maintain the reagent mixing beads in positions that are spaced apart from the movable mixing element.

Some embodiments described herein may include a method for measuring coagulation characteristics of a blood sample. The method may include detecting a blood testing cartridge being inserted into a receiver portion of a blood testing control unit. The method may also include prompting a user for input via a user interface of the blood testing control unit to initiate automated transport of blood in the blood sample reservoir to one or more blood testing chambers within the cartridge for measuring viscoelastic characteristics of the blood in each of the blood testing chambers. The method may further include automatically transporting to each of the one or more blood testing chambers within the cartridge a predetermined amount of a blood sample from a blood sample receiver of the blood testing cartridge.

Some or all of the embodiments described herein may provide one or more of the following advantages. First, some embodiments of the thromboelastometry system are configured to be automated so that user interactions with the system are minimized. As a result, human resources—especially in a point-of-care context like a surgical theater—can be utilized with greater efficiency. The reduction of user interactions can also reduce the chances for manual operator errors, such as measuring inaccuracies, reagent mixing errors, and the like. Accordingly, more accurate thromboelastometry results may be attained in some circumstances.

Second, in some embodiments, the cartridge component includes multiple fluid channels that are each individually controllable so that multiple different assays can be performed from a single supply of a blood sample. For example, each fluid channel includes a dedicated valve and a dedicated vent that are controllable by the analyzer console so that the blood flow and testing of each fluid channel is individually controllable. This feature enables the thromboelastometry system to automatically perform sophisticated assay processes.

Third, in some embodiments, the analyzer console can be configured to perform a number of quality-control operations/confirmations so as to ensure the blood test results are not compromised. For example, the analyzer console can be configured to verify the blood testing cartridge is heated to a target temperature (e.g., about 37° C.) prior to the blood sample being distributed to testing chambers of the cartridge. Because temperature of the blood sample can affect the coagulation characteristics in some circumstances, the accuracy of the thromboelastometry results may be enhanced as a result of such temperature-control operations/confirmations.

Fourth, in particular embodiments of the cartridge device, the geometry of the blood flow paths through the fluid channels of the cartridge are configured to reduce the potential for disturbing the blood (e.g., causing bubble formation, etc.), and/or damaging the blood, in a manner that may negatively impact the accuracy of the blood test results.

Fifth, in some embodiments, the blood testing cartridge (and, optionally, the blood collection reservoir) can be equipped with one or more computer-readable components so as to promptly transfer relevant information of the analyzer console for each blood sample testing cycle. For example, each cartridge can be labeled with a barcode, near-field communication tag, and RFID tag, or the like that includes information such as, but not limited to, the types of assays to be performed by the cartridge, the type of reagents container within the cartridge, manufacturer information, an expiration date, or the like. In such embodiments, the analyzer console can include a barcode reader (or a reader for a near-field communication tag, a RFID tag, or the like) that scans the barcode upon insertion of the cartridge into the analyzer console. The analyzer console automatically performs appropriate actions in response to the data read from the barcode. In another example, each blood collection reservoir that is to be used with a corresponding cartridge can be labeled with a barcode, near-field communication tag, and RFID tag, or the like that includes information such as, but not limited to, patient information, clinician information, calibration information, or the like (e.g., which is readable by a corresponding reader device of the analyzer console).

Sixth, each fluid pathway of the cartridge can include a mixing chamber with one or more reagents and a mixing element located therein. In some embodiments, the reagents comprise dissolvable reagent beads. The mixing chambers of the cartridge can be configured to inhibit the mixing element from direct contact with the reagent beads. Additionally, the mixing chambers may be configured prevent blood leakages from prematurely dissolving reagent beads and/or configured to direct the flow of blood and control the sequence of dissolving the reagent beads. Further advantages associated with the thromboelastometry systems provided herein are also envisioned, as will be evident from the following disclosure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A, 1B, 2, and 3 are perspective illustrations depicting the components and use of an example thromboelastometry system, in accordance with some embodiments.

Like reference symbols in the various drawings indicate like elements.

DETAILED DESCRIPTION OF ILLUSTRATIVE EMBODIMENTS

Figure 3:
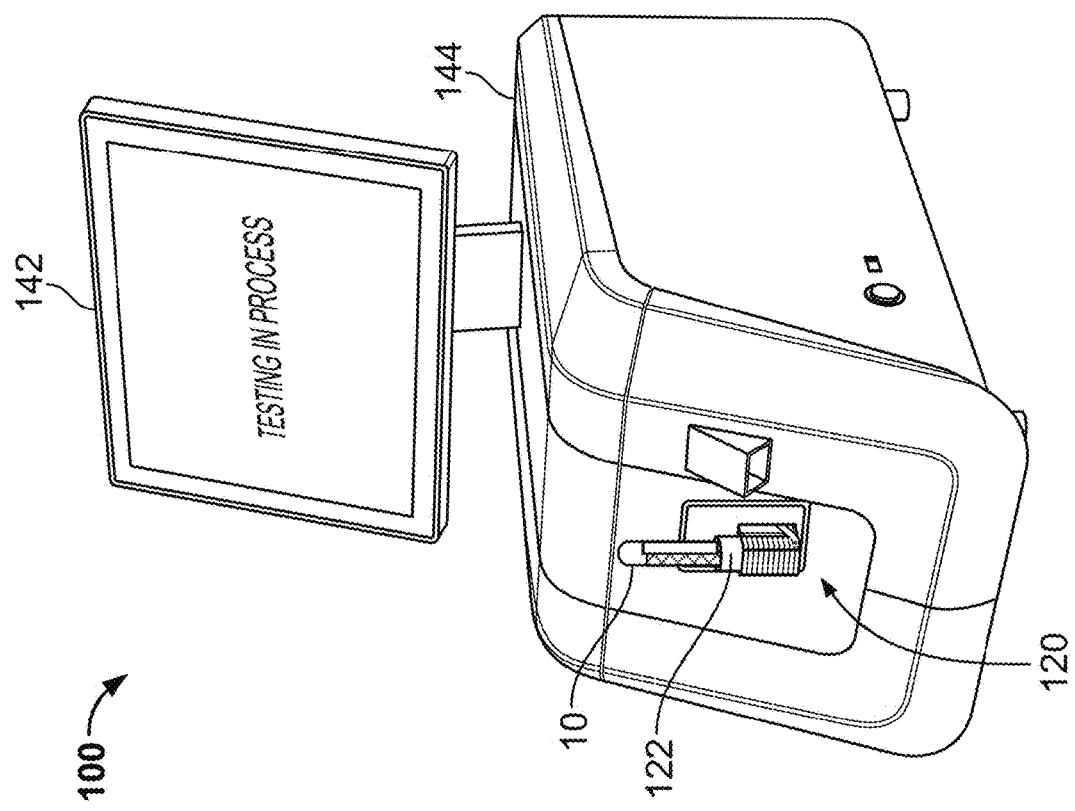

Referring to FIGS. 1A-3, some embodiments of a blood testing system 100 include an analyzer console 140 and one or more cartridges 120 configured to releasably mate with analyzer console 140. In this embodiment, the blood testing system 100 is a thromboelastometry system that is configured to determine a number of blood coagulation characteristics of a blood sample input into the cartridge 120. For example, the cartridge 120 can be configured as a single-use cartridge that includes a blood sample receiver 122 for mating with a blood sample reservoir 10 (e.g., a vacutainer sample tube supplied by Becton, Dickinson & Company of Franklin Lakes, NJ, or another blood reservoir structure). In some cases, an adapter may be used to couple other types of blood sample reservoirs 10 with the cartridge 120 (e.g., tubing may be used through which blood can be injected into the cartridge 120, and the like). The thromboelastometry system 100 can be used as a whole blood coagulation analysis system that is particularly advantageous at a point-of-care site (e.g., in a surgical theater while a patient is undergoing or preparing for surgery, or the like). Additionally, thromboelastometry system 100 can be used as a whole blood coagulation analysis system in a laboratory setting.

The analyzer console 140 includes a user interface 142 (with touchscreen display in this embodiment) and a main chassis 144. The user interface display 142 can be configured to output one or more graphical results 143 from the blood testing assays performed via the cartridge 120 and console 140 (e.g., one or more plots, such as those sometimes refer to as a TEMogram, numeric data or measurements, or a combination thereof). In some embodiments, the user interface display 142 is rigidly attached to the analyzer console 140. In particular embodiments, the user interface display 142 is pivotable and/or is otherwise positionally adjustable in relation to the main chassis 144. A main power switch 148 can be located at a convenient but protected location on the main chassis 144.

In the depicted embodiment, the touchscreen display 142 is configured to receive user input and to display output information to the user. For example, the user can enter information to the thromboelastometry system 100 by making selections of various soft-buttons that may be displayed on the touchscreen display 142 at times during the beginning, middle, and end of the testing process. In some embodiments, other selections such as, but not limited to, soft keyboard entries can be provided via touchscreen display 142. In some embodiments, data entry can be performed additionally or alternatively by voice entry. In other embodiments, the user interface may include other peripheral devices can be included (e.g., a mouse, a keyboard, an additional display device, and the like) as part of the thromboelastometry system 100. In some embodiments, a computer data network (e.g., intranet, internet, LAN, etc.) may be used to allow for remote devices to receive and/or input information from the system 100. For example, in some embodiments one or more remote displays can be utilized via network connections. In the depicted embodiment, the thromboelastometry system 100 also includes an external barcode reader 146. The external barcode reader 146 can facilitate convenient one-dimensional or two-dimensional barcode entry of data such as, but not limited to, blood sample data, user identification, patient identification, normal values, and the like. Alternatively or additionally, the thromboelastometry system 100 can be equipped with a reader configured to read near-field communication tags, RFID tags, or the like.

In the depicted embodiment, the main chassis 144 houses various internal sub-systems (as described further below), includes various electronic connection receptacles (not shown), and includes a cartridge port 150. The various electronic connection receptacles can include network and device connectors such as, but not limited to, one or more USB ports, Ethernet ports (e.g., RJ45), VGA connectors, Sub-D9 connectors (RS232), and the like. Such connection receptacles can be located on the rear of the main chassis 144, or at other convenient locations on the main chassis 144. For example, in some embodiments one or more USB ports may be located on or near the front of the main chassis 144. A USB port, so located, may provide user convenience for recording data onto a memory stick, for example. In some embodiments, the thromboelastometry system 100 is configured to operate using wireless communication modalities such as, but not limited to, Wi-Fi, Bluetooth, NFC, RF, IR, and the like.

Still referring to FIGS. 1A-3, the cartridge port 150 can be located at a readily accessible location on the main chassis 144. In the depicted embodiment, the cartridge port 150 is located on the front of the main chassis 144 so that it is conveniently accessible by a user in a point-of-care site. The cartridge port 150 defines an opening and internal space that is shaped complementarily to the outer dimensions of the single-use cartridge 120. To insert the single-use cartridge 120 into the cartridge port 150, the user can grasp the end of the cartridge 120 that includes the blood sample receiver 122 and slide in the opposite end (leading end) into the cartridge port 150. The sliding insertion can continue until a hard-stop is reached that defines the fully inserted position. In the fully inserted position, a trailing end portion (including the blood sample receiver 122 in this embodiment) of the single-use cartridge 120 remains exterior to the main chassis 144. The portion of the cartridge 120 that is received into the cartridge port 150 can include outer surface features (such as a tapered angle a rear end portion shown in FIG. 1B) that mate with at least one internal interface element inside the console 140 to ensure correct positioning of the cartridge 120. As such, at least the blood sample receiver 122 remains exterior to the main chassis 144 throughout the duration of the blood sample testing. In this configuration, the blood sample receiver 122 serves as a blood sample well that is accessible so that the blood sample reservoir 10 can be inserted into the receiver 122 while the single-use cartridge 120 is mated with the console 140 in the fully inserted position. In some embodiments, the cartridge port 150 and the main chassis 144 are configured so that the exposed portion of the cartridge 120 is protected from inadvertent contact. As described further below, an internal sensor (e.g., a microswitch, an optical sensor, etc.) can detect when the single-use cartridge 120 has been fully inserted into the main chassis 144.

When the analyzer console 140 has detected that the cartridge 120 has been fully inserted, in some embodiments the analyzer console 140 initiates one or more of the following actions. An internal cartridge clamping mechanism that includes positioning pins can be activated to accurately position and releasably retain the single-use cartridge 120 in the fully inserted position. One or more cartridge heating elements can be activated to warm the cartridge 120. The temperature of the cartridge 120 can be monitored. A barcode on the leading end of the cartridge 120 can be read and the barcode data can be stored in memory of the analyzer console 140. One or more blood detection sensors can inspect the cartridge 120 for the presence of blood (which should not be present at this time). The rotational thromboelastometry measuring sub-system can be engaged with the cartridge 120 and, optionally, rotation of the rotary thromboelastometry measuring sub-system can begin (without the presence of blood). The cartridge 120 can be leak tested using vacuum or air pressure delivered by the analyzer console 140. For example, a pressure/vacuum decay test can be performed. In some embodiments, other actions can be additionally or alternatively activated when the analyzer console 140 has detected that the cartridge 120 has been fully inserted. After the completion of such actions, in some embodiments an indication of the results of the actions may be displayed on the touchscreen display 142 (e.g., pass or fail). If the analyzer console 140 determines that the actions were completed successfully, a prompt can be provided on the touchscreen display 142 that informs the user that the thromboelastometry system 100 is ready to receive the blood sample reservoir 10.

Briefly, in some embodiments a user can operate the depicted thromboelastometry system 100 embodiment as follows. First, the user can insert the single-use cartridge 120 into the cartridge port 150 so that the cartridge 120 is placed into the fully inserted position. Completion of that step will automatically initiate a series of operations by the thromboelastometry system 100 as described below. Upon successful completion of such operations, a notification that the blood collection tube 10 can be inserted into the sample well 122 will be displayed on the touchscreen display 142. After the user has mated the blood collection tube 10 into the sample well 122, the user initiates testing by pressing a "start" button (or the like) on the touchscreen display 142. At least the blood measuring, reagent mixing, and thromboelastometry testing is performed automatically by the system 100 thereafter (e.g., without requiring manual intervention from the user in this embodiment). When the testing is completed, the results are displayed on the touchscreen display 142 in the form of qualitative graphical representations and quantitative parameters (e.g., as depicted in FIG. 1A). Also, when the testing is completed, the cartridge 120 can be removed from the console 140 and discarded (e.g., the cartridge 120 in such embodiments is not reusable in that the reagent beads (described below) are no longer present in the cartridge and the measurement chambers contain the clotted blood sample portions).

Alternately, in some embodiments the blood collection tube 10 can be inserted into the sample well 122 of the cartridge 120 prior to insertion of the cartridge 120 into the cartridge port 150. In such circumstances, the blood from the collection tube 10 may not advance to the measurement chambers (described below) of the blood cartridge 120 until after the console 140 acts upon the cartridge 120 (again, as described below). With the blood collection tube 10 being pre-coupled with the cartridge 120, the combination of the blood collection tube 10 and the cartridge 120 can then be inserted into the cartridge port 150.

Figure 4:
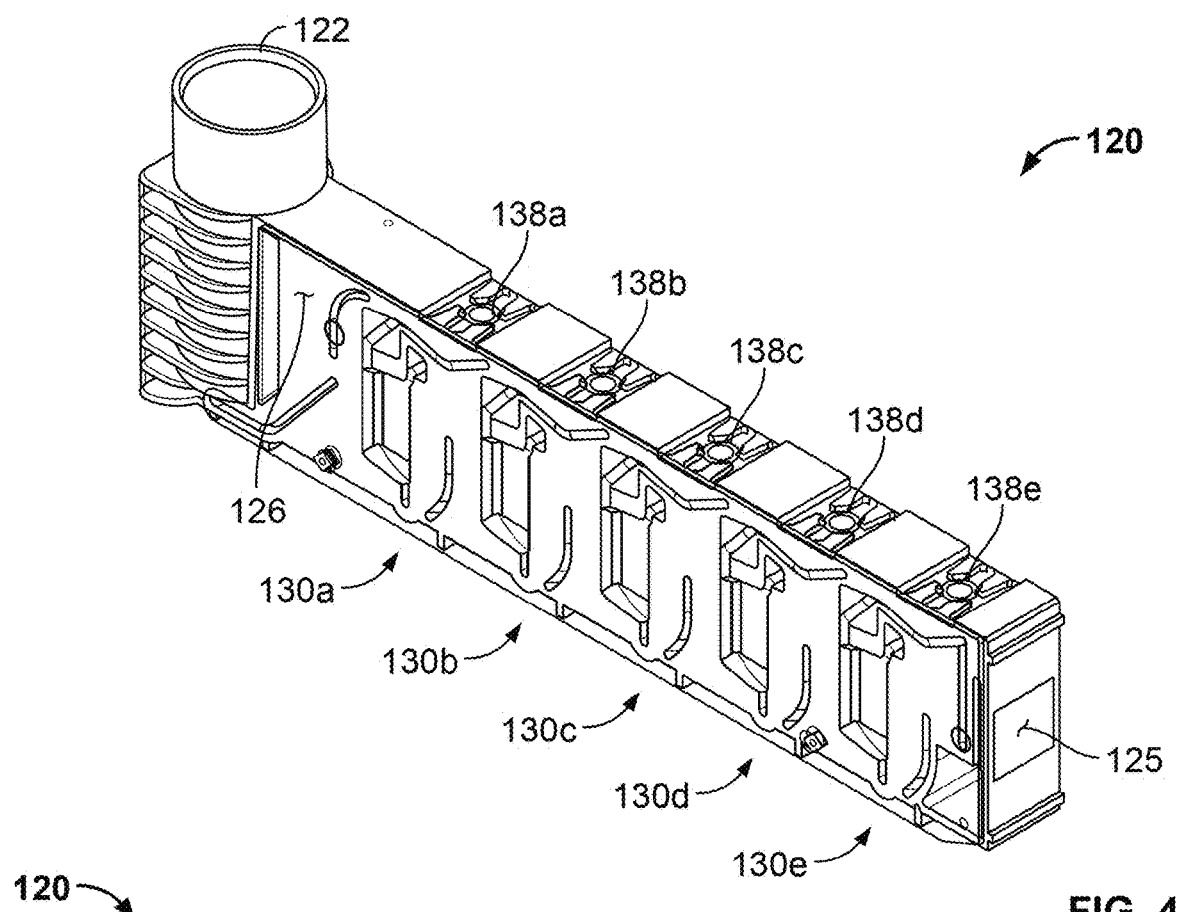
FIG. 4 is a perspective view of the example cartridge component of the thromboelastometry system of FIGS. 1A, 1B, 2, and 3.
Figure 5:
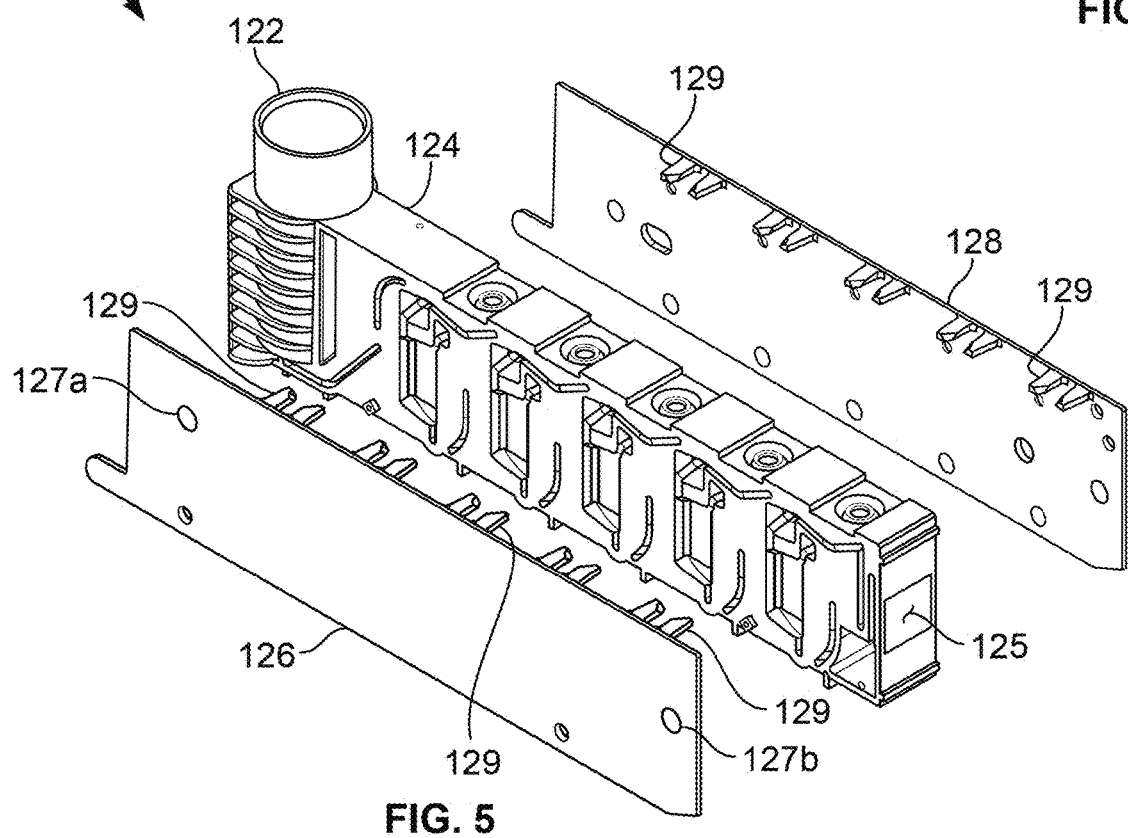
FIG. 5 is an exploded view of the cartridge component of FIG. 4.

Referring now to FIGS. 4 and 5, the depicted embodiment of the single-use cartridge 120 includes a main body 124, a right cover 126, a left cover 128, and five pins 138a, 138b, 138c, 138d, and 138e. The right cover 126 is affixed to right side of the main body 124, and the left cover 128 is affixed to the left side of the main body 124. As such, the right and left covers 126 and 128 enclose cavities and flow channels of the main body 124 to define blood flow paths as described further below. The aforementioned sample well 122 is part of the main body 124. However, other constructions of the single use cartridge 120 are also envisioned.

In some embodiments, the main body 124, right cover 126, left cover 128, and the pins 138a, 138b, 138c, 138d, and 138e are made by injection molding. After molding, the right and left covers 126 and 128 can be affixed to the main body 124 using various techniques including, but not limited to, ultrasonic welding, laser welding, solvent bonding, adhesive bonding, UV curable adhesive bonding, and the like. Various polymeric materials can be used to construct the main body 124, right cover 126, left cover 128, and pins 138a-e. For example, such polymeric materials can include, but are not limited to acrylic, polycarbonate, polyvinyl chloride (PVC), polyethylene, polypropylene, polymethyl methacrylate, polystyrene, acrylonitrile butadiene styrene (ABS), polyethylene, polypropylene, and the like, and combinations thereof. In some embodiments, the materials are used to construct the main body 124, right cover 126, left cover 128, and pins 138a-e comprise an acrylic-based multi-polymer compound. In some embodiments, the main body 124, right cover 126, and left cover 128 are essentially transparent, or at least translucent. Therefore, in FIG. 4, features of the main body 124 are visible even though the right cover 126 is attached thereto.

Figure 8:
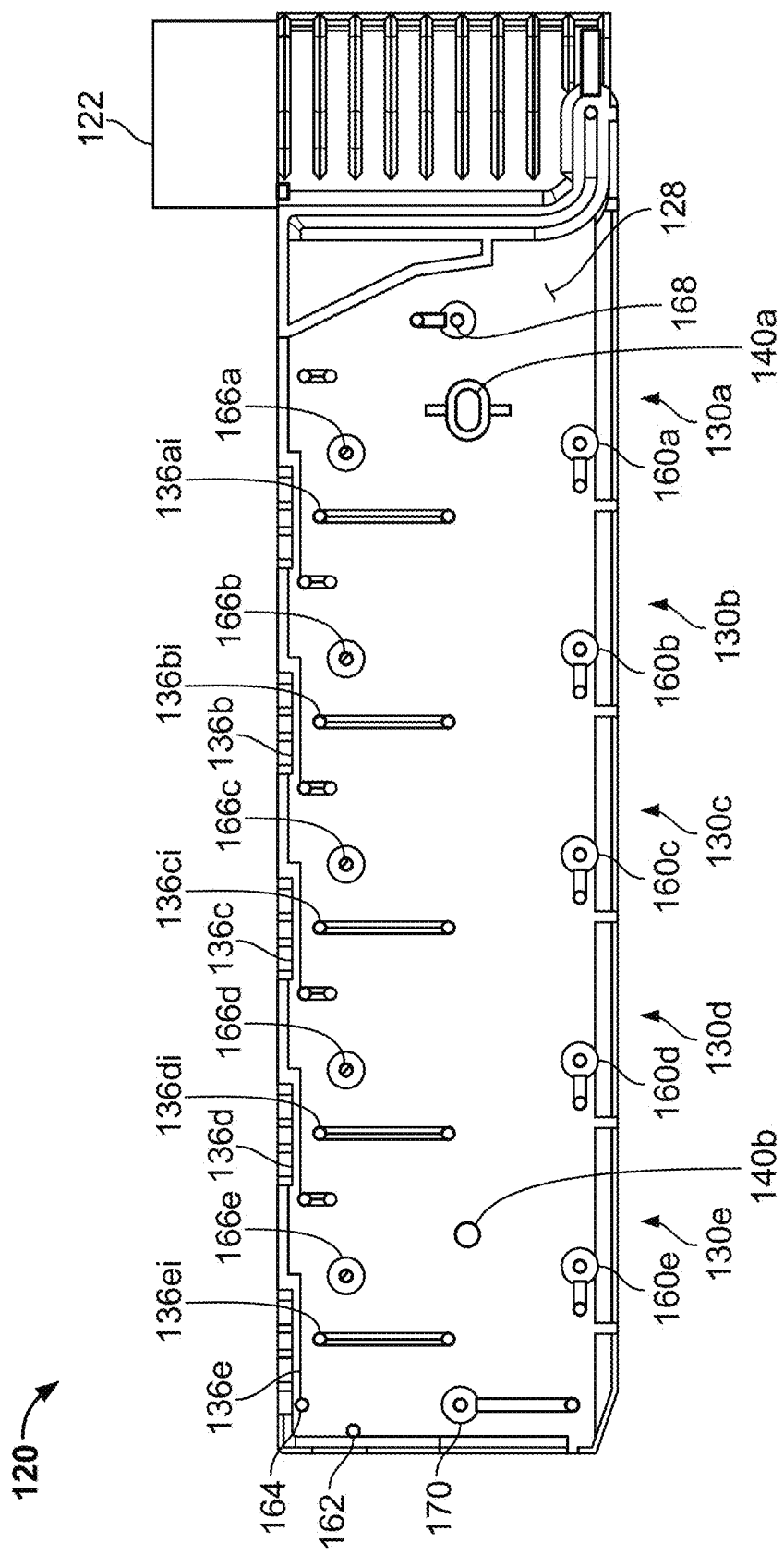
FIG. 8 is a left side view of the cartridge component of FIG. 4.

In some embodiments, overmolding, such as by insert molding or multi-shot molding techniques, may be used to construct some aspects of the main body 124, right cover 126, and/or left cover 128 (i.e., a device component). For example, elastomeric valve elements (as described further below) may be overmolded in the left cover 128. To generate valves by overmolding, a first mask is used to generate a device component without valves. The mask is an inverse of the shape of the device component, the device component including open spaces for later insertion of valves. A polymer is poured into the first mask to form a hard plastic device component. Then a second mask having the inverse of the shape of the device component with the valves is provided. The hardened plastic device component is placed in the mask, and an elastomeric material is injected into the open spaces formed in the device component by the first mask, thereby forming elastomeric valves in the device component. In some embodiments, the device component is the main body 124, right cover 126, and/or left cover 128. Exemplary valves 160a-e, 168, and 170 in a left cover 128 formed by overmolding are shown in FIG. 8. In some embodiments, the valves comprise an elastomeric material, deformable upon application of pressure. Deformation of the valves by application of external pressure pushes the elastomeric material into the duct, thereby fluidically sealing the duct to prevent flow of a sample liquid through the duct.

Further, in some embodiments secondary operations may be performed to the cartridge 120. For example, one or more needles 123a-b (refer to FIG. 6) for piercing a blood collection tube may be installed within the sample well 122 using secondary operations.

The single-use cartridge 120 also includes the five pins 138a, 138b, 138c, 138d, and 138e. The pins 138a-e are individual component parts (e.g., refer to FIG. 10B) that are retained within openings of the main body 124 (e.g., within testing chambers 136a-e (sometimes referred to as "cups") as described further below in connection with FIGS. 8A-10B). Tabs 129, located on the right and left covers 126 and 128, mechanically retain the pins 138a-e in the main body 124. However, the pins 138a-e are free to move within the confines of the main body 124 to a limited extent. For example, the pins 139a-e are free to rotate uninhibitedly within the main body 124 and to translate vertically by few millimeters. This configuration of the pins 138a-e in relation to the other components of the cartridge 120 can be created as follows. Prior to affixing the right and left covers 126 and 128 to the main body 124, the pins 138a-e can be placed within their respective locations in the main body 124 as shown in FIG. 5. With the pins 138a-e positioned in the main body 124, the right and left covers 126 and 128 can then be affixed to the main body 124. With the right and left covers 126 and 128 affixed to the main body and the pins 138a-e positioned in the main body 124, the pins are secured in place vertically by the tabs 129 over the top of the pin 138a-e such that they cannot fall out or be removed from the cup 136a-e without removal of the right and left covers 126 and 128 from the main body 124. The tabs 129 allow free rotational movement of the pin 138a-e, as well as sufficient vertical motion to allow the pin 138a-e to interact with a fluid sample to perform a measurement of viscoelastic characteristics of a fluid sample in the cup 136a-e, e.g., rotational thromboelastometry. In addition, the tabs 129 provide an opening for a shaft 310b to couple with a pin 138b, as shown in FIG. 10C. In one example, the right and left covers 126 and 128 are affixed to the main body 124 and thereafter the pins 138a-e are pushed into the main body 122 past the tabs 129. The tabs 129 of the right and left covers 126 and 128 will block the pins 138a-e from falling out of the main body 122, even if the cartridge 120 is turned upside down. In some embodiments, the pin and tabs are positioned to prevent escape of semi-coagulated fluid sample in the testing chamber from escaping the testing chamber, even if the cartridge 120 is turned upside down.

Figure 2:
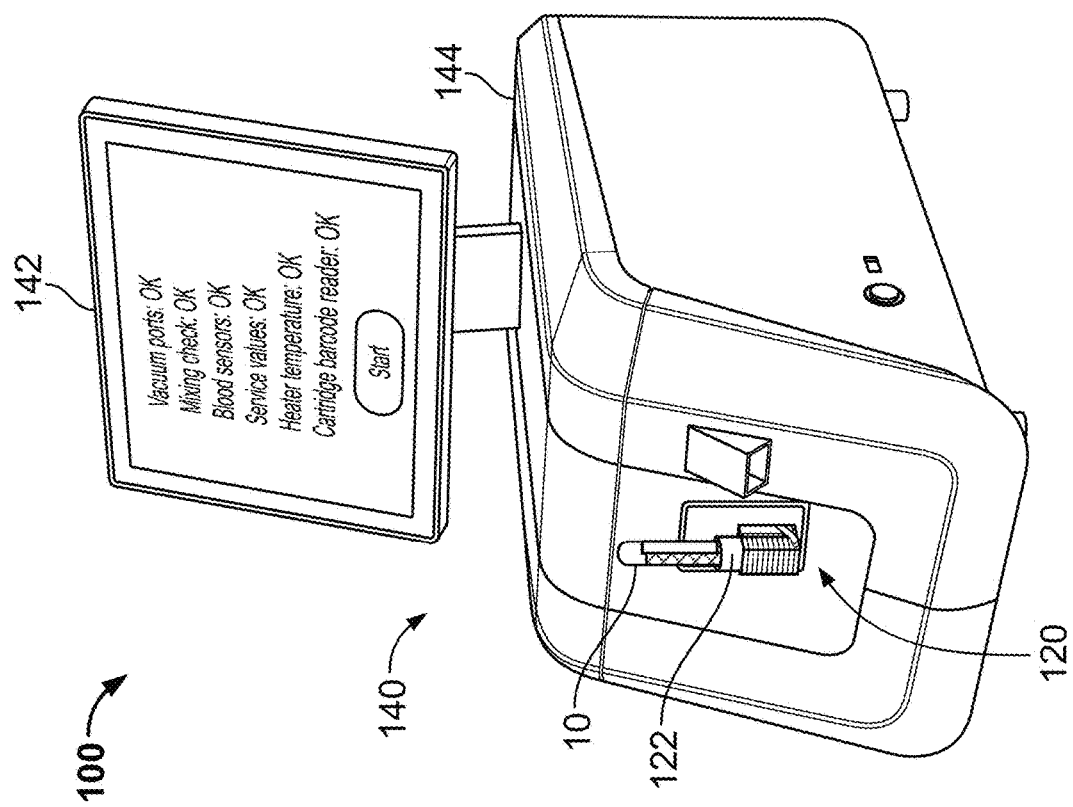

In some embodiments, the main body 124 includes a barcode location 125. The barcode location 125 can be used as a location at which to adhere a barcode label, or to print a barcode. The barcode location 125 is on the leading end of the cartridge 120 (in relation to the direction of insertion of the cartridge 120 into the analyzer console 140 as shown in FIGS. 1-3).

In the depicted embodiment, the right cover 126 includes blood detection locations 127a and 127b. As will be described further below, the blood detection locations 127a and 127b are designated locations on the cartridge 120 at which sensors of the analyzer console 140 interface with the cartridge 120. The sensors inspect for the presence of blood within the cartridge 120 at the blood detection locations 127a and 127b. In some embodiments, the sensors are optical sensors (e.g., infrared sensors) and the blood detection locations 127a and 127b are polished areas that have enhanced transparency and optical clarity. As such, the right cover 126 is configured so that the optical sensors of the analyzer console 140 can readily detect the presence or absence of blood at the blood detection locations 127a and 127b.

Figure 6:
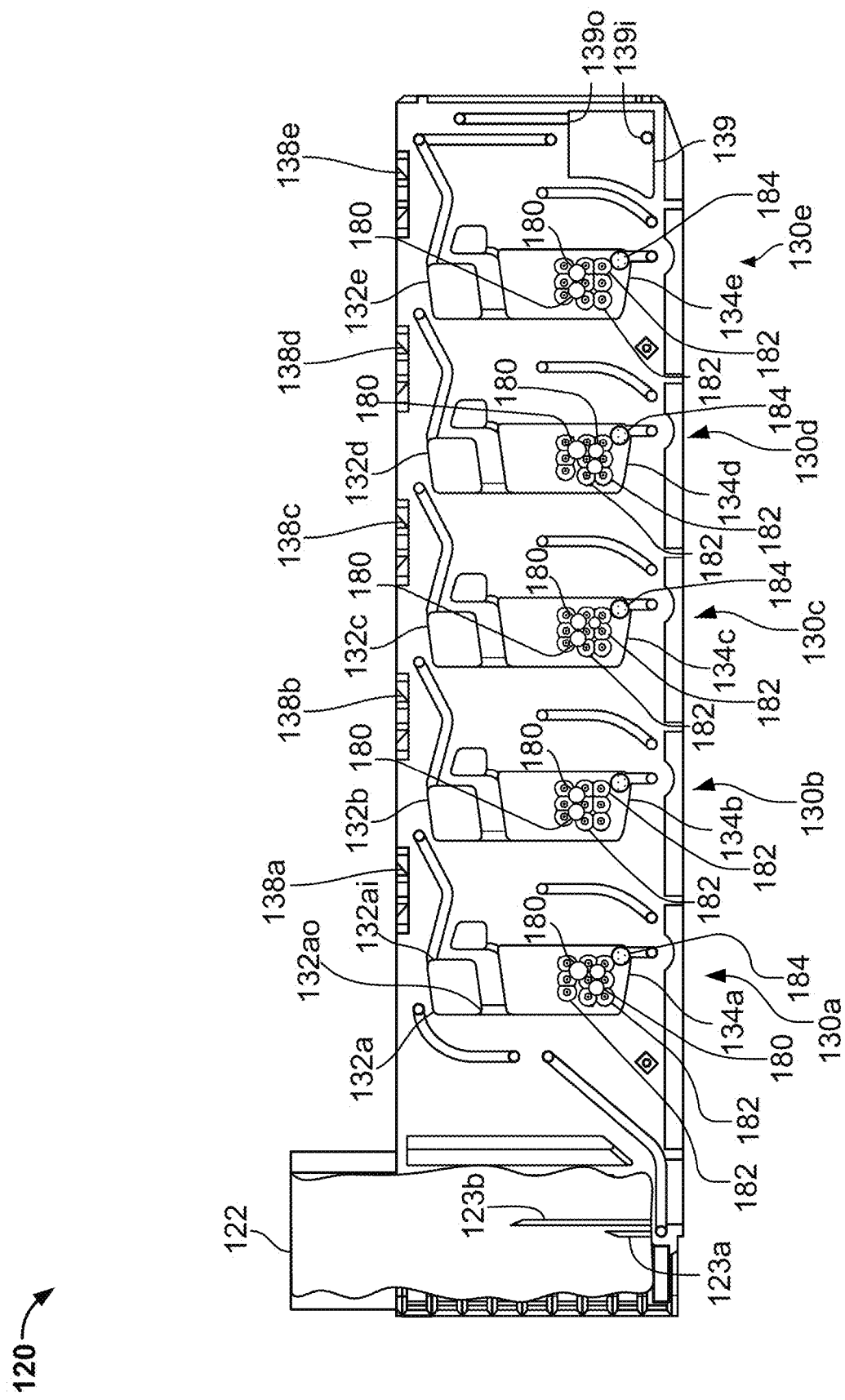
FIG. 6 is a right side partial cutaway view of the cartridge component of FIG. 4.

Referring now to FIGS. 4, 5, and 6, broadly speaking the single-use cartridge 120 is configured to: (i) extract blood from a blood collection tube (e.g., blood collection tube 10 of FIGS. 1-3) and measure a precise volume of the extracted blood, (ii) mix a precise amount of blood with reagents, and (iii) deliver the mixture to multiple cup and pin locations of the cartridge 120 where thromboelastometry testing is performed. These steps will be described in more detail below.

In the depicted embodiment, the single-use cartridge 120 includes five individual blood flow channels 130a, 130b, 130c, 130d, and 130e. Alternately, in some embodiments the cartridge includes a single individual blood flow channel, or two individual blood flow channels, or three individual blood flow channels, or four individual blood flow channels, or six individual blood flow channels, or more than six individual blood flow channels. Each channel 130a-e includes: (i) a measuring chamber, (ii) a mixing chamber containing reagent(s) and a mixing element, and (iii) a blood coagulation testing chamber (e.g., in this embodiment a cup having a movable probe/pin therein). For example, the channel 130a includes a measuring chamber 132a, a mixing chamber 134a, and a testing chamber 136a (refer to the example of the testing chamber being depicted in detail in FIGS. 9A-D). Similarly, the channel 130b includes a measuring chamber 132b, a mixing chamber 134b, and a testing chamber 136b; the channel 130c includes a measuring chamber 132c, a mixing chamber 134c, and a testing chamber 136a; the channel 130d includes a measuring chamber 132d, a mixing chamber 134d, and a testing chamber 136d; and the channel 130e includes a measuring chamber 132e, a mixing chamber 134e, and a testing chamber 136e.

In some embodiments, the sample well 122 includes needles 123a and 123b that are configured to pierce a septum of a blood collection tube when the blood collection tube is inserted into the sample well 122. The needle 123a is in fluid communication with the channels 130a-e, while the needle 123b is a vent that facilitates the ready flow of blood out of the blood collection tube.

In the depicted embodiment, the fluid flow paths from the needle 123a to the channels 130a-e are as follows. The needle 123a is confluent with the measuring chamber 132a. The measuring chamber 132a is confluent with the measuring chamber 132b. The measuring chamber 132b is confluent with the measuring chamber 132c. The measuring chamber 132c is confluent with the measuring chamber 132d. The measuring chamber 132d is confluent with the measuring chamber 132e. Accordingly, blood can flow out of the blood collection tube through the needle 123a to the measuring chamber 132a; from the measuring chamber 132a to the measuring chamber 132b; from the measuring chamber 132b to the measuring chamber 132c; from the measuring chamber 132c to the measuring chamber 132d; and from the measuring chamber 132d to the measuring chamber 132e. The measuring chambers 132a-e may also be referred to as metering chambers 132a-e. Each measuring chamber 132a-e has an inlet port and an outlet port. The inlet ports are located near the top of the measuring chambers 132a-e. For example, measuring chamber inlet port 132ai is located near the top of the measuring chamber 132a. This configuration can be advantageous if the blood contains gaseous bubbles, because such gas may be allowed to escape from the blood as the blood enters the measuring chambers 132a-e. In addition, this configuration may advantageously minimize fluid flow turbulence as the blood flows into the measuring chambers 132a-e, thereby reducing the likelihood of damaging the blood cells.

The outlet ports 132ao-eo for transferring blood from the measuring chambers 132a-e to the mixing chambers 134a-e are located at the bottom of the measuring chambers. For example, measuring chamber outlet port 132ao is located at the bottom of the measuring chamber 132a. In some embodiments, the bottom of the measuring chamber 132a is angled downward towards the outlet port 132ao. In some embodiments, the bottom of the measuring chamber 132a is at an angle of 2°-15° from a plane parallel to the bottom or top of the cartridge 120. In some embodiments, the bottom of the measuring chamber 132a is at an angle of 2°-15° from a plane orthogonal to the direction of force applied to move the blood sample through the outlet port 132ao. In one embodiment, the angles described above are approximately 2°, 3°, 4°, 5°, 6°, 7°, 8°, 9°, 10°, 11°, 12°, 13°, 14°, or 15°. In a preferred embodiment, the angles described above are 5°, although other angles will also be effective. This configuration can help facilitate the complete filling of the measuring chambers 132a-e with blood. It can also minimize transfer of bubbles into the outlet port 132ao as more blood is transferred to the outlet port 132ao before the surface of the volume of blood (which may contain bubbles) contained in the measuring chamber 132a contacts the outlet port 132ao. As such, a precise volume of blood is contained within the measuring chambers 132a-e.

In some embodiments, the top of the measuring chamber 132a is angled to cause air to escape the measuring chamber 132a from a transfer port located at the top of the measuring chamber opposite to the inlet port 132ai. The transfer port is used to transfer air and fluid out of the measuring chamber 132a and into another measuring chamber (e.g., 132b) or into an overflow chamber 139. In this embodiment, the top of the measuring chamber 132a is angled upward from a low point above an inlet port 132ai to a higher point above the transfer port. The angle of the top of the measuring chamber is between 2°-15° when compared to the a plane parallel to the bottom or top of the device, or as compared to a plane orthogonal to the major field of gravitational force applied to the blood sample while in the measuring chamber 132a. In one embodiment, the angle described above is approximately 2°, 3°, 4°, 5°, 6°, 7°, 8°, 9°, 10°, 11°, 12°, 13°, 14°, or 15°. In a preferred embodiment, the angle described above is 5°, although other angles will also be effective. In a device comprising the angled top of the measuring chamber 132a, air and bubbles are transferred out of the measuring chamber 132a before blood, providing a measured blood sample with decreased amount of air that may impact the accuracy of the measurement of the blood, as well as interfere with other downstream applications. In some embodiments, both the top and bottom of the measuring chamber 132a are angled as described above.

From the foregoing description of the fluid flow paths from the needle 123a to the measuring chambers 132a-e, and from the foregoing description of the location of the measuring chamber outlet ports, it should be understood that the measuring chambers 132a-e will be filled with blood in a sequential manner. That is, first measuring chamber 132a will be filled with blood; then blood from measuring chamber 132a will flow to measuring chamber 132b; then measuring chamber 132b will be filled with blood; then blood from measuring chamber 132b will flow to measuring chamber 132c; then measuring chamber 132c will be filled with blood; then blood from measuring chamber 132c will flow to measuring chamber 132d; then measuring chamber 132d will be filled with blood; then blood from measuring chamber 132d will flow to measuring chamber 132e; then measuring chamber 132e will be filled with blood.

After the measuring chamber 132e is filled with blood, then blood from measuring chamber 132e will flow to an overflow chamber 139. The blood flowing from measuring chamber 132e will enter the overflow chamber 139 at an overflow chamber inlet port 139i. As will be described further below, the overflow chamber 139 serves to ensure that the measuring chamber 132e becomes completely full, while preventing blood from exiting the cartridge 120 and flowing into a vacuum source that is used to draw the blood into the measuring chambers 132a-e as described above. The vacuum source is fluidly connected to the overflow chamber 139 at an overflow chamber outlet port 139o. When a negative pressure (with respect to ambient pressure) from the vacuum source is applied at the overflow chamber outlet port 139o, blood from a blood collection tube that is coupled with needle 123a will flow into the cartridge 120 to fill all the measuring chambers 132a-e. Some blood will also exit the measuring chamber 132e and flow towards the overflow chamber 139.

As described further below, various valves and vents are interspersed within the fluid flow paths so that the blood flow can be controlled by the analyzer console according to predefined schemes. In addition, the aforementioned blood detection locations 127a and 127b (refer to FIG. 5) are designated locations on the cartridge 120 at which sensors of the analyzer console 140 interface with the cartridge 120. The sensors inspect for the presence of blood within the cartridge 120 at the blood detection locations 127a and 127b. The blood sensor location 127a is on the fluid flow path between the needle 123a and the measuring chamber 132a. When the analyzer console detects blood at blood sensor location 127a, the analyzer console 140 determines that blood has been drawn into the cartridge 120. The blood sensor location 127b is on the fluid flow path between the measuring chamber 132e and the overflow chamber 139. When the analyzer console detects blood at blood sensor location 127b, the analyzer console 140 determines that blood has been drawn into and filled all the measuring chambers 132a-e. Further, when the analyzer console 140 detects blood at blood sensor location 127b, the analyzer console 140 may cease further application of negative pressure at the overflow chamber outlet port 139o. In other words, by detecting blood at blood sensor location 127b, the analyzer console 140 can determine that the application of vacuum has successfully filled all the measuring chambers 132a-e and that the application of vacuum can be ceased. Optionally, the cartridge 120 may be equipped with a blood temperature sensor at or near the location of blood sensor location 127b so as to verify the blood sample is at a predetermined target temperature.

As described above, each individual channel 130a-e has a measuring chamber 132a-e respectively. In some embodiments, the fluid flow paths within the individual channels 130a-e are as follows. From the measuring chambers 132a-e, the blood can flow to the respective mixing chambers 134a-e. For example, the blood from measuring chamber 132a can flow to the mixing chamber 134a. Similarly, the blood from measuring chamber 132b can flow to the mixing chamber 134b; the blood from measuring chamber 132c can flow to the mixing chamber 134c; the blood from measuring chamber 132d can flow to the mixing chamber 134d; and the blood from measuring chamber 132e can flow to the mixing chamber 134e. From the mixing chambers 132a-e (after completion of the mixing), the blood can flow to the respective testing chambers 136a-e (having a corresponding probe/pin 138a-e therein, refer below to FIG. 10A-b). For example, the blood from mixing chamber 134a can flow to the testing chamber 136a. Similarly, the blood from mixing chamber 134b can flow to the testing chamber 136b; the blood from mixing chamber 134c can flow to the testing chamber 136c; the blood from mixing chamber 134d can flow to the testing chamber 136d; and the blood from mixing chamber 134e can flow to the testing chamber 136e. Various valves and vents that are controllable by the analyzer console 140 are interspersed within the fluid flow paths of the individual channels 130a-e. Using such valves and vents, the blood flow within the individual channels 130a-e can be controlled by the analyzer console 140 in accordance with predefined schemes.

Figure 7A:
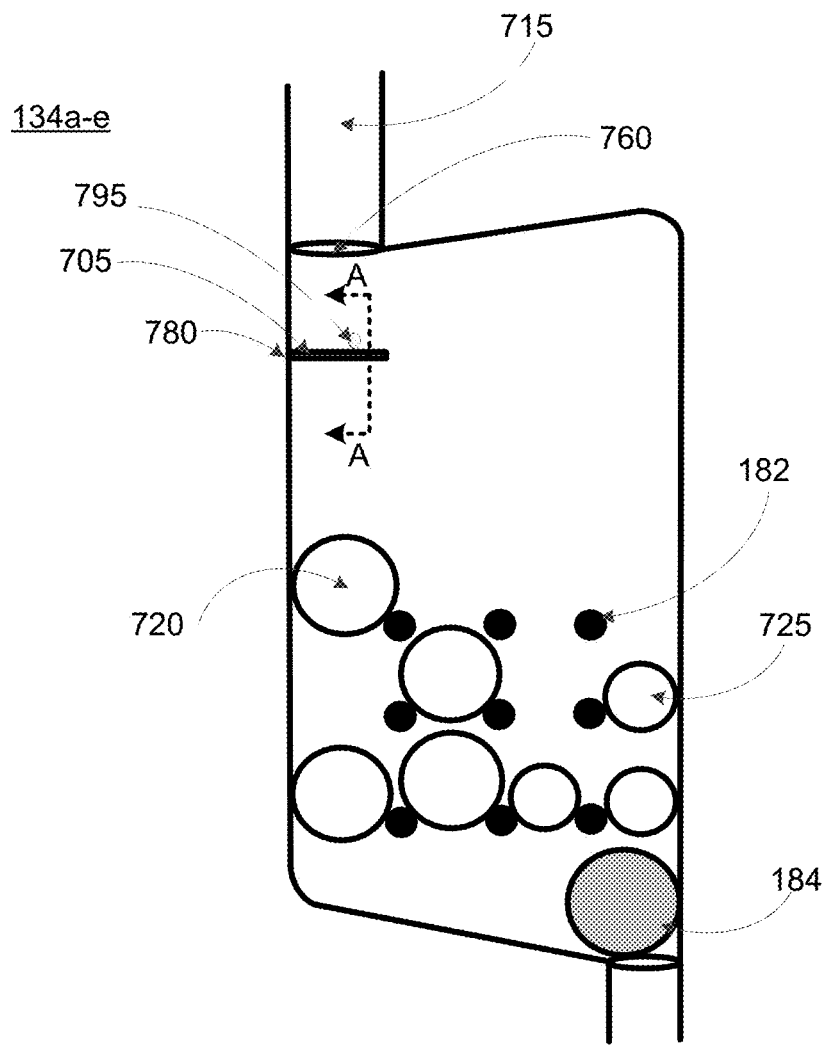
FIG. 7A is a close-up view of a mixture chamber with a leak barrier within the cartridge component.
Figure 7B:
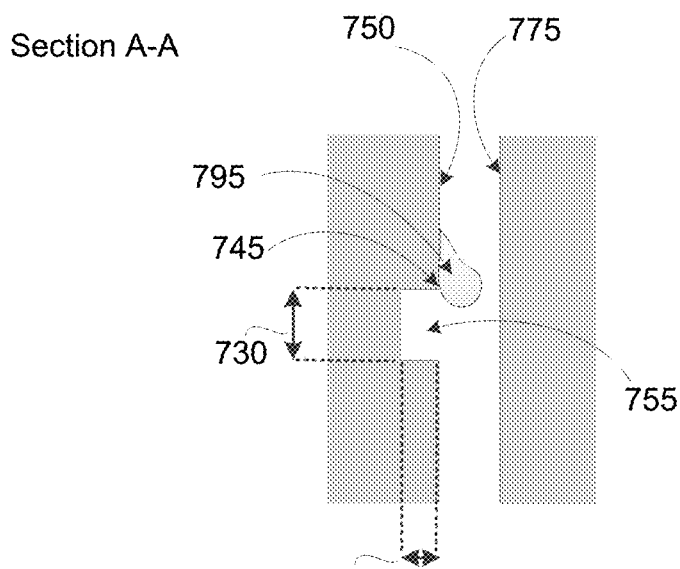
FIG. 7B is a side view of a leak barrier configured to stop blood leakage in the mixture chamber.
Figure 7C:
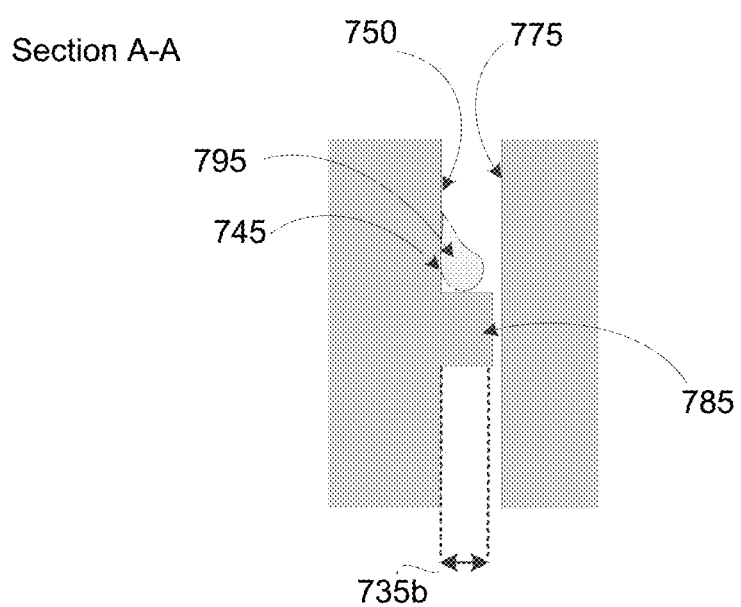
FIG. 7C is a side view of a leak barrier that is elevated above a wall.
Figure 7D:
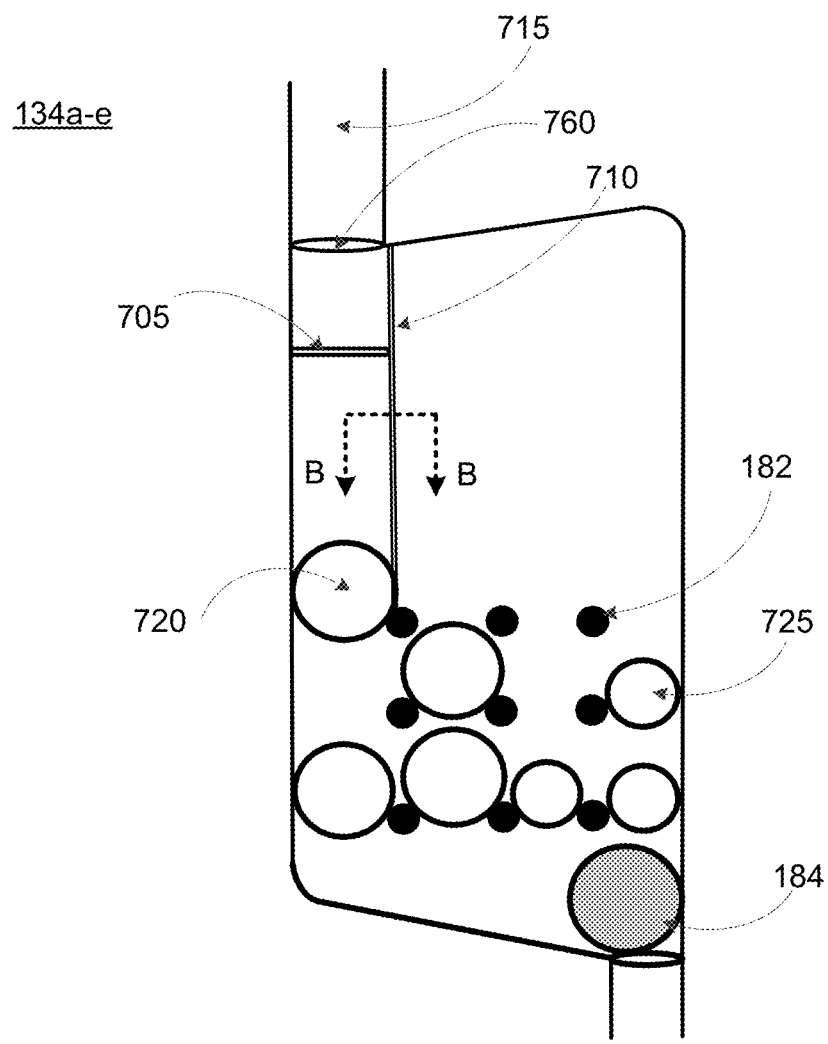
FIG. 7D is a close-up view of a mixture chamber with a leak barrier and a blood guide.

FIGS. 6 and 7A-7F show additional features specifically pertaining to the mixing chambers 134a-e of the blood cartridge device, according to some embodiments. Some embodiments of the mixing chambers 134a-e contain: (i) one or more dissolvable reagent beads 180 (see FIG. 6), (ii) multiple retaining elements 182, and (iii) a mixing element 184. Additionally, some embodiments of the mixing chambers 134a-e may also include a leak barrier 705 (see FIG. 7A) and one or more blood guides 710 (see FIG. 7D). In various embodiments, the leak barrier 705 and the one or more blood guides 710 are formed on a wall of the right cover 126 such that when the right cover 126 is assembled with the main body 124 of the blood cartridge device, the leak barrier 705 and one or more blood guides are located in the mixing chambers 134a-e as depicted in FIGS. 7A and 7D, respectively. Therefore, FIGS. 7A and 7D depict a view of the mixing chamber 134a-e of the blood cartridge device with the right cover 126 assembled with the main body 124. In other embodiments, the leak barrier 705 and the one or more blood guides 710 are formed on a wall of the mixing chamber 134a-e.

Duct 715 is present for each of the mixing chambers 134a-e, and the duct 715 connects each mixing chamber 134a-e to the corresponding measuring chamber 132a-e such that blood can flow from the measuring chamber 132a-e through the duct 715 to the mixing chamber 134a-e.

Figure 7E:
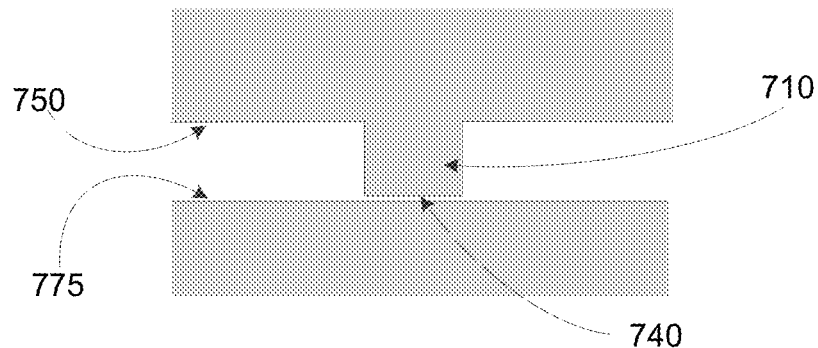
FIG. 7E is a side view of a blood guide configured to direct the flow of blood in the mixture chamber.
Figure 7F:
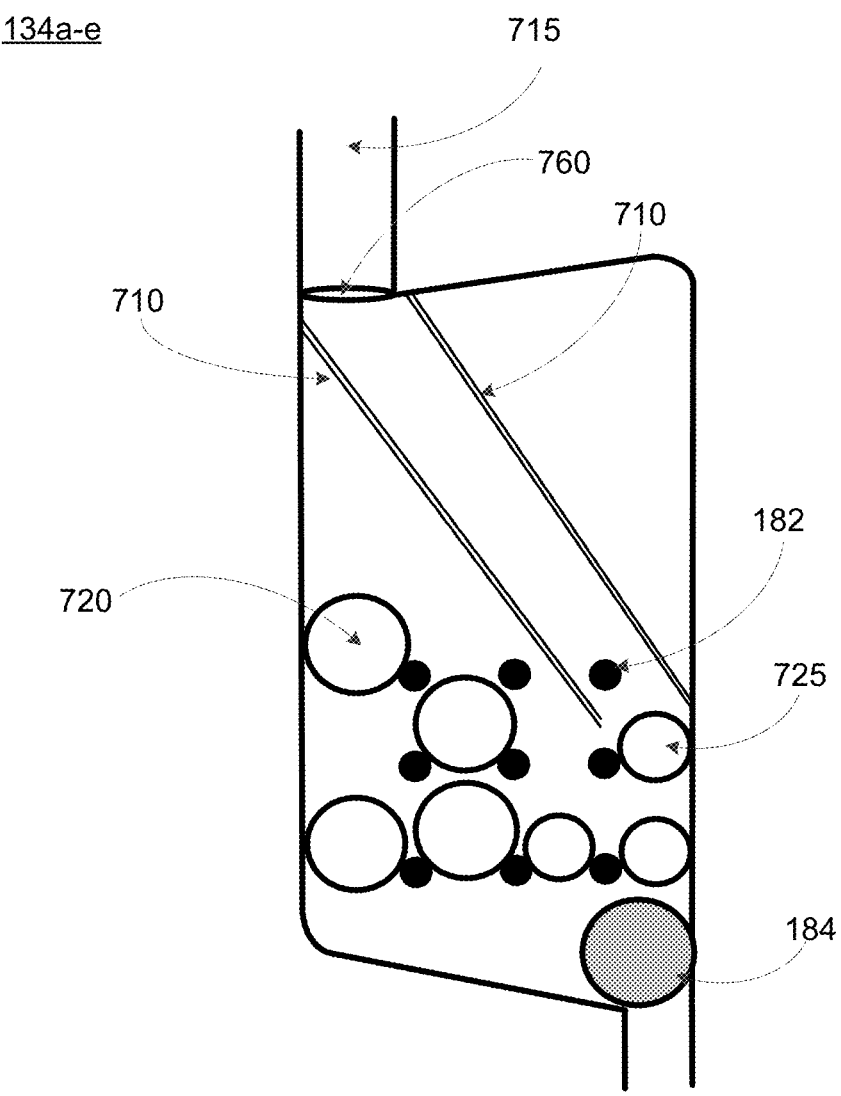
FIG. 7F is a close-up view of a mixture chamber with multiple blood guides for directing blood flow to a dissolvable reagent bead.

As depicted in FIG. 6, one or more dissolvable reagent beads 180 are disposed within and retained within the confines of the multiple retaining elements 182. FIGS. 7A, 7D, and 7F each illustrate an embodiment that includes two different types of reagent beads including a first type of reagent bead 720 and second type of reagent bead 725. The term "dissolvable reagent beads 180" or "reagent beads" referred to hereafter includes both the first type of reagent bead 720 and second type of reagent bead 725.

The mixing elements 184 are disposed in the bottom portions of the mixing chambers 134a-e, and are free to move horizontally across the bottom portions of the mixing chambers 134a-e. The multiple retaining elements 182 separate the reagent beads 180 from the mixing element 184, and prevent the mixing element 184 from migrating upward away from the bottom portions of the mixing chambers 134a-e. Thus, the multiple retaining elements 182 prevent direct contact of the mixing element 184 with reagent beads 180 in the mixing chambers 134a-e. In an embodiment, the retaining elements 182 extend into each mixing chamber 134a-e so as to maintain a predetermined vertical position of each of the reagent beads 180 within the mixing chamber (e.g., a vertical position below the height of the blood portion passed into the mixing chamber 134a-e), thereby ensuring that each of the beads 180 will be submerged when the predetermined amount of blood is directed into the respective mixing chamber 134a-e. In an embodiment, the height of the liquid that fills the mixing chamber 134a-e from the measuring chamber 132a-e (i.e., the fill level) is above the retaining elements 182 in the mixing chamber. In some embodiments, the retaining elements 182 are above the height of the fill level of the mixing chamber. In these embodiments, the retaining elements are configured to position the reagent in the path of the fluid such that the reagent is dissolved by the liquid upon entry of the liquid into the mixing chamber. In some embodiments, the flow path is defined as the path the liquid travels to go from one chamber to another, including within the chamber itself after entering from the duct 715.

Also, in some embodiments, the multiple retaining elements 182 in each mixing chamber 134a-e maintain each of the reagent beads 180 in the respective mixing chamber 134a-e separate from one another. In such embodiments, each of the reagent beads 180 is not contacted by other beads 180 in the respective mixing chamber 134a-e, is not contacted by the mixing element 184 in the respective mixing chamber 134a-e, and is maintained at a vertical height within the respective mixing chamber 134a-e below the height of the blood portion transported into the respective mixing chamber 134a-e.

The retaining elements 182 may take the form of several unique configurations that result in control over the location of the reagent beads 180. In some embodiments, the retaining elements 182 also prevent contact between different reagent beads 180, contact of reagent beads 180 with the mixing element 184, and/or contact of the reagent beads 180 with other surfaces or components in the mixing chamber 134a-e. In some embodiments, the retaining element 182 is configured to limit movement of the reagent bead 180 within the mixing chamber 134a-e and configured to allow the sample liquid or blood sample to dissolve the reagent bead 180. In some embodiments, the retaining element 182 comprises a barrier. The retaining element 182 can also comprise an inward protrusion or an outward protrusion in the wall of the mixing chamber 134a-e or on the surface of a right cover 126 or left cover 128, or on other surfaces of the device. In some embodiments, the retaining element 182 comprises a channel, a vertical or horizontal track, a post, or a divot. The retaining element 182 may comprise an array of posts or an array of divots. For example, FIGS. 7A, 7D, and 7F each depict an array of posts (e.g. retaining elements 182) that are spaced evenly in the mixing chamber 134a-e. In some embodiments, the array of posts comprises posts of different diameters to hold reagent beads of different diameters. Additionally, the array of posts need not be spaced equidistantly relative to one another. In some embodiments, the retaining element 182 comprises a compartment or a series of compartments for holding a reagent bead. The retaining element 182 can also be configured to both limit the movement of a reagent bead in the mixing chamber 134a-e, and to allow blood to flow in a way that it contacts and dissolves the reagent bead 180. In some embodiments, the retaining element 182 is configured to allow flow of a blood sample through the mixing chamber 134a-e.

The retaining element 182 can further secure the reagent bead 180 below a predetermined blood sample fill level in the mixing chamber 134a-e. This fill level is determined by the volume of blood provided by the measuring chamber 132a-e, and by the dimensions of the mixing chamber 134a-e and volume of components or reagents within the mixing chamber 134a-e at the time of filling. This fill level can be predetermined based on the above factors. Therefore, the retaining elements 182 are specifically designed to maintain the position of the reagent beads 180 below this predetermined fill level.

Additionally, the retaining elements 182 can limit the movement of a mixing element 184 within the mixing chamber 134a-e. In some embodiments, the resting element 182 used to restrict movement of a mixing element 184 within the mixing chamber 134a-e comprise an array of posts or a compartment that allows a sample fluid or blood sample in the mixing chamber 134a-e to contact the mixing element 184 such that the sample fluid or blood sample is agitated to facilitate dissolving reagents within the mixing chamber 134a-e.

In the depicted embodiment, the one or more dissolvable reagent beads 180 are spherical and are of two different sizes (e.g., about 2 mm diameter and about 3 mm diameter). The two differently sized reagent beads are depicted in FIGS. 7A, 7D, and 7F as reagent beads 720 and 725. However, the use of other shapes and/or sizes of reagent beads 180 may be readily envisioned. In some embodiments, the reagent beads 180 are lyophilized materials, but other forms of materials may also be envisioned. The reagent beads 180 can comprise materials such as, but not limited to, $CaCl_2$, ellagic acid/phospholipids, tissue factor, heparinase, polybrene, cytochalasin D, tranexamic acid, and the like, and combinations thereof. The reagent beads 180 are dissolvable in blood. For example, in this particular embodiment, each of the five mixing chambers 134a-e is configured to mix a predetermined volume of blood (as defined by the respective measurement chamber 132a-e) with a different reagent composition (from the one or more reagent beads 180 therein) for purposes of performing five different assays. In this example, the first mixing chamber 134e may include multiple reagent beads 180 such as $CaCl_2$) and ellagic acid/phospholipids for mixing with the predetermined volume of blood (from the corresponding measuring chamber 132e) so that the first sample portion can be used in a first type of assay. Also in this example, the second mixing chamber 134d may include multiple reagent beads 180 that provide $CaCl_2$), ellagic acid/phospholipids, and heparinase for mixing with the predetermined volume of blood (from the corresponding measuring chamber 132d) so that the second sample portion can be used in a second type of assay. Further, in this example, the third mixing chamber 134c may include multiple reagent beads 180 that provide $CaCl_2$), tissue factor, and polybrene for mixing with the predetermined volume of blood (from the corresponding measuring chamber 132c) so that the third sample portion can be used in a third type of assay. Also in this example, the fourth mixing chamber 134b may include multiple reagent beads 180 that provide $CaCl_2$), tissue factor, polybrene, and cytochalasin D for mixing with the predetermined volume of blood (from the corresponding measuring chamber 132b) so that the fourth sample portion can be used in a fourth type of assay. Lastly, in this example, the fifth mixing chamber 134a may include multiple reagent beads 180 that provide $CaCl_2$), tissue factor, polybrene, and tranexamic acid for mixing with the predetermined volume of blood (from the corresponding measuring chamber 132a) so that the fifth sample portion can be used in a fifth type of assay.

In some embodiments, the reagent bead 180 carrying the $CaCl_2$) reagent is separated from the rest of the beads 180 in the respective mixing chamber 134a-e so as to first allow mixing and then activation/clotting of the a citrated blood sample. Such separation of the reagent bead 180 carrying the $CaCl_2$) reagent may be achieved using the retaining elements 182 (as described above). Alternatively, such separation can be achieved by retaining the reagent bead 180 carrying the $CaCl_2$) reagent in a separate channel or separate mixing chamber that is separated from other beads 180 in the respective chamber 134a-e (such that the blood portion reaches the $CaCl_2$) reagent after the blood portion mixes with other beads 180 within the respective mixing chamber 134a-e). Alternatively, such separation can be achieved by positioning a $CaCl_2$) reagent liquid or a dried-film $CaCl_2$) reagent in a different location in the mixing chamber 134a-e so that the blood portion reaches the $CaCl_2$) reagent after the blood portion mixes with other beads 180 in the respective mixing chamber 134a-e. As a specific example, the $CaCl_2$) carrying beads may be located on the right side of the mixing chamber 134a-e, distant from the duct 715 where blood enters into the mixing chamber 134a-e. Alternatively, the reagent bead 180 carrying the $CaCl_2$) reagent can be coated with an extra layer (and then retained by the retaining elements 182 as described above) so that the blood portion begins to dissolve the reagent bead 180 carrying the $CaCl_2$) reagent after the blood portion previously mixes with other beads 180 within the respective mixing chamber 134a-e.

Other configurations for providing a reagent to the blood sample may also be used. In some embodiments, a reagent is coated on the wall of a mixing chamber 134a-e. In some embodiments, a reagent is coated on the wall of the right cover 126 or the left cover 128 such that when the right cover 126 or left cover 128 is assembled with the main body 124 of the blood cartridge device, the reagent is at least partially or entirely contained within the mixing chamber 134a-e. In some embodiments, the reagent is coated so that it remains under the fill level of the mixing chamber 134a-e (the fill level pertaining to the height of blood in the mixing chamber as determined in part by the predetermined volume of blood as measured in the measuring chamber). In some embodiments, the coated reagent is a film layer, i.e., a reagent film. A reagent film is a layer of reagent coated on or near a surface. The reagent film may be liquid or may be dried. A liquid reagent may be retained as a film layer by a dissolvable layer of material placed over the liquid reagent. A liquid reagent layer may also be applied and then dried on the surface. A pre-dried or solid film reagent may also be applied to a surface to form a film layer. In some embodiments, the film layer is in the form of a dissolvable film strip. In some embodiments, certain reagents are preferred to be delivered in a reagent film as opposed to a reagent bead 180. For example, certain reagents that are difficult to lyophilize in a reagent bead 180 may instead be applied on or near a surface in the device as a film layer.

In some embodiments, the coated reagent is in the form of reagent beads 180. Reagent beads may be secured to the wall of a chamber or to a cover using retaining elements 182. The retaining elements 182 may comprise a series of compartments, posts, divots, inward or outward protrusions, or an array of any of the above. Other shapes or configurations of reagent that can be coated or secured to the cover, a wall of a chamber, or within a fluidic passage between chambers, are also envisioned. In some embodiments, both reagent beads 180 and reagent film are coated on one or more surfaces of the device, e.g., in the mixing chamber 134a-e.

A reagent film may also be provided to dissolve in a blood sample in the mixing chamber 134a-e. The reagent film is dissolvable in blood. The reagent film is adhered to a surface in the mixing chamber 134a-e. In some embodiments, a reagent film is deposited on the walls of the mixing chamber 134a-e. In some embodiments, a reagent film is deposited on the right cover 126 or the left cover 128 at a region that at least partially covers or forms a wall of the mixing chamber 134a-e. The reagent film may be used alone, or in addition to one or more reagent beads 180 placed in the mixing chamber 134a-e. Thus, the use of one or more reagent films in a mixing chamber 134a-e provides additional mechanisms of introducing a reagent into a mixing chamber 134a-e to dissolve in the blood.

In some embodiments, the reagent film comprises a lyophilized material, but other forms of materials are also envisioned. The reagent film can comprise materials such as, but not limited to $CaCl_2$), ellagic acid/phospholipids, tissue factor, heparinase, polybrene, cytochalasin D, tranexamic acid, and the like, and combinations thereof. In one particular example, each of the five mixing chambers 134a-e is configured to mix a predetermined volume of blood (as defined by the respective measurement chamber 132a-e) with a different reagent composition (from one or more reagent beads 180 and/or one or more reagent films therein). In this example, the first mixing chamber 134e may include multiple reagent beads 180 and at least one reagent film to provide $CaCl_2$) and ellagic acid/phospholipids for mixing with the predetermined volume of blood (from the corresponding measuring chamber 132e) so that the first sample portion can be used in a first type of assay. Also in this example, the second mixing chamber 134d may include multiple reagent beads 180 and at least one reagent film to provide $CaCl_2$), ellagic acid/phospholipids, and heparinase for mixing with the predetermined volume of blood (from the corresponding measuring chamber 132d) so that the second sample portion can be used in a second type of assay. Further, in this example, the third mixing chamber 134c may include multiple reagent beads 180 and at least one reagent film to provide $CaCl_2$), tissue factor, and polybrene for mixing with the predetermined volume of blood (from the corresponding measuring chamber 132c) so that the third sample portion can be used in a third type of assay. Also in this example, the fourth mixing chamber 134b may include multiple reagent beads 180 and at least one reagent film to provide $CaCl_2$), tissue factor, polybrene, and cytochalasin D for mixing with the predetermined volume of blood (from the corresponding measuring chamber 132b) so that the fourth sample portion can be used in a fourth type of assay. Lastly, in this example, the fifth mixing chamber 134a may include multiple reagent beads 180 and at least one reagent film to provide $CaCl_2$), tissue factor, polybrene, and tranexamic acid for mixing with the predetermined volume of blood (from the corresponding measuring chamber 132a) so that the fifth sample portion can be used in a fifth type of assay.

Further, a reagent film may be deposited on surfaces upstream or downstream from the mixing chamber to mix with the blood sample before or after the mixing chamber. In some embodiments, a reagent film carrying the $CaCl_2$) reagent is placed in a separate channel or separate mixing chamber that is separated from other reagent beads 180 or reagent film in the respective chamber 134a-e (e.g., such that the blood portion reaches the $CaCl_2$) reagent film after the blood portion mixes with other reagent beads 180 and/or reagent films within the respective mixing chamber 134a-e). Alternatively, a $CaCl_2$) reagent film may be deposited in the mixing chamber 134a-e and coated with an extra dissolvable film layer so that the blood portion begins to dissolve the other reagent film carrying the $CaCl_2$) reagent after the blood portion previously mixes with other reagent beads 180 or reagent films within the respective mixing chamber 134a-e.

In some embodiments, the reagent bead 180 or reagent film is separated from the rest of the reagent beads 180 or reagent film in the respective mixing chamber 134a-e so as to allow mixing with different reagents in a preferred sequence. In one embodiment, such separation of the reagent bead 180 may be achieved using the retaining elements 182 (as described above). Alternatively, such separation can be achieved by retaining the reagent bead 180 or reagent film in a separate channel or separate mixing chamber that is separated from other beads 180 or reagent films in the respective chamber 134a-e (such that the blood portion reaches and mixes with the loaded reagents in a preferred sequence). In one embodiment, such separation can be achieved by positioning a reagent liquid, reagent bead 180 or a dried-film reagent in a separate channel so that the blood portion reaches the reagent before or after the blood portion mixes with other reagent beads 180 or reagent films in the respective mixing chamber 134a-e. In some embodiments, the reagent bead 180 or reagent film is placed along a duct 715 fluidically connecting the mixing chamber 134a-e and the testing chamber 136a-e. Alternatively, the reagent bead 180 or reagent film can be coated with an extra layer (and then retained by the retaining elements 182 as described above) so that the blood portion begins to dissolve the reagent in the reagent bead 180 or reagent film comprising an additional dissolvable layer after the blood portion previously mixes with other reagent beads 180 or reagent films within the respective mixing chamber 134a-e. In some embodiments, the coated reagent layer is a dissolvable film layer manufactured from a substrate including a polymeric composition and a reagent. The polymeric composition forms a dissolvable barrier to maintain the coating of the reagent on or near a surface in the device. Upon contact with a blood sample, the polymeric composition dissolves to allow the blood sample to mix with the reagent.

As depicted in FIGS. 7A, 7D, and 7F, the mixing chamber 134 a-e includes a mixing element 184 which comprises a ferromagnetic material including, but not limited to, nickel, cobalt, chromium (IV) oxide, gadolinium, permalloy, and alnico (an aluminum-nickel-cobalt alloy) and the like, and combinations thereof. In the depicted embodiment, the mixing element 184 is spherical and is solid. In other embodiments, the mixing element 184 may have a shape such as, but not limited to, cubical, conical, cylindrical, fan-shaped, elongated, prismatic, and the like, as well as irregular shapes. In some embodiments, the mixing element 184 may include one or more surface features such as protrusions, indentations, or holes, and the like.

The mixing elements 184 are movable within the mixing chambers 134a-e in response to movement of magnets with which the mixing elements 184 magnetically couple. The magnets that the mixing elements 184 magnetically couple with are contained within the analyzer console 140. The movement of the mixing elements 184 encourages the reagent beads 180 to dissolve in the blood contained within the mixing chambers 134a-e.

Referring to FIG. 7A, the mixing chambers 134a-e may further include design configurations that are responsible for controlling the flow of blood in the mixing chambers 134a-e. Further reference will be made to FIG. 7B, which depicts a rotated side view, termed Section A-A, of the leak barrier 705. Section A-A shows the leak barrier 705 in a right-to-left manner along the dotted arrows in FIG. 7A.

For example, FIG. 7A depicts a leak barrier 705 located directly below the duct 715 that fluidically connects the measuring chambers 132a-e and the mixing chambers 134a-e. When the measuring chamber 132a-e is filled with blood, a blood leakage may enter the mixing chamber 134a-e from the duct 715 due to gravitational forces. More specifically, the duct 715 outputs into the entrance 760 of the mixing chamber 134a-e. Leaked blood that enters the mixing chamber 134a-e may prematurely contact the dissolvable reagent beads 180, thereby causing them to crystallize and to perform poorly in blood testing assays. Therefore, the leak barrier 705 is configured to stop blood that may leak from the measuring chambers 132a-e to prevent premature contacting of the dissolvable reagent beads 180 by the leaked blood. In various embodiments, the leak barrier 705 is an indentation in the wall of either the mixing chamber 134a-e or the right cover 126. In other embodiments, the leak barrier 705 may be an elevated ridge that extends outward from a wall of the mixing chamber 134a-e or a wall of the right cover 126. As used hereafter, the phrase "wall of a blood cartridge device" will be used to reference a wall of the mixing chamber 134a-e or a wall of the right cover 126; more specifically, the wall of the right cover 126 closes off the mixing chamber 134a-e when the right cover 126 is assembled with the main body 124.

In various embodiments, leaked blood flows downward from the entrance 760 of the mixing chamber 134a-e and contacts a top edge 745 (see FIG. 7B) of the leak barrier 705, the leak barrier 705 being an indentation on the right cover 126. The leak barrier 705 may stop the leaked blood entirely or the leak barrier 705 may direct the blood towards a side 780 of the mixing chamber 134a-e. The side 780 of the mixing chamber extends upward from a wall of the mixing chamber 134a-e and contacts a wall of the right cover 126 when the right cover 126 is assembled with the main body 124 of the blood cartridge device. In various embodiments, the elevated surface of the side 780 of the mixing chamber 134a-e includes crevices between the elevated surface of the side 780 of the mixing chamber 134a-e and a wall of the right cover 126 or left cover 128. Therefore, the leak barrier 705 directs leaked blood to the crevices located at the interface of the side 780 of the mixing chamber 134a-e and the wall of the right cover 126. This prevents the leaked blood from proceeding into the lower part of the mixing chamber 134a-e.

Referring to FIG. 7B, a small amount of leaked blood 795 may gather at the top edge 745 of the leak barrier 705 and stop traveling in a downward direction. Multiple factors cause the leaked blood 795 to be stopped or directed by the leak barrier 705 to the side 780 of the mixing chamber 134a-e. For example, the intrinsic high viscosity of blood, in combination with the intrinsic high surface tension of blood, contribute towards the cohesiveness of the leaked blood. The cohesion forces of the leaked blood cause it to remain at the top edge 745 of the leak barrier 705, thereby preventing the leaked blood from traveling further downward into the mixing chamber 134a-e.

The leaked blood 795 may also experience adhesive forces or capillary action (e.g., capillary forces). In some embodiments, the adhesive forces are due to the adhesion of the leaked blood 795 to both the wall 750 of the right cover 126 and the wall 775 of the mixing chamber 134a-e. In other embodiments, the adhesive forces are due to the adhesion of the leaked blood 795 to only the wall 750 of the right cover 126.

The adhesive forces may cause the leaked blood to preferably flow horizontally along the wall 750 of the right cover 126 (as opposed to over the leak barrier 705) to reach the crevices located at the side 780 of the mixing chamber 134a-e. At a minimum, the high viscosity of blood, the high surface tension of blood, and the adhesive forces combine to enable the leak barrier 705 to stop the leaked blood 795 and/or direct the leaked blood 795 towards a side 780 of the mixing chamber 134a-e.

In other embodiments, upon contacting the leak barrier 705, the leaked blood enters into the leak barrier 705 and may be retained in the leak barrier 705 due to the intrinsic factors of the blood. For example, the intrinsic high viscosity of blood prevents the leaked blood from leaving the leak barrier 705 and further traveling downward into the mixing chamber 134a-e. Additionally, once the leaked blood resides in the leak barrier 705, the intrinsic surface tension of blood resists the gravitational force, thereby preventing any blood from leaving the indentation 755. Thirdly, the leaked blood experiences capillary action (e.g., capillary forces) due to the walls of the leak barrier 705, which prevents further blood flow down into the mixing chamber 134a-e.

In various embodiments, the leak barrier 705 may be further coated with a substance to encourage the capturing of leaked blood by the leak barrier 705. For example, the surfaces next to the top edge 745 of the leak barrier 705, may be coated with a hydrophilic substance to encourage leaked blood to enter into the leak barrier 705. The bottom edge of the leak barrier 705, namely the edge of the leak barrier 705 that is farthest from the duct 715, may be coated with a hydrophobic substance to discourage leaked blood from leaving the leak barrier 705.

When it is desired to fill the mixing chamber 134a-e, the respective vent 166a-e (see FIG. 8) is opened to enable flow of blood through the duct. In this scenario, the blood, given its overall volume entering into the mixing chamber 134a-e, overcomes the leak barrier 705 and flows into the bottom of the mixing chamber 134a-e where the dissolvable reagent beads 180 reside. In other words, the leak barrier 705 is designed to stop small volumes (e.g., droplets) of blood but does not stanch the flow of large volumes of blood within the mixing chamber 134a-e. The amount of blood that a leak barrier 705 is able to retain before allowing blood flow into the mixing chamber 134a-e is dependent on the viscosity of the blood and the surface tension of the blood. For example, higher blood viscosity would correspond to a higher threshold volume of blood that may be retained by the leak barrier 705 because of the slow flow of the blood. Alternatively, blood with a lower viscosity requires a lower threshold volume to overcome the leak barrier 705 as the low viscosity blood would flow more rapidly. Similarly, blood with a higher surface tension would correspond to a higher threshold volume of blood. Given that the surface tension of blood is dependent on environmental temperature, the environmental temperature may be altered to control surface tension, and therefore, control the threshold volume required to overcome the leak barrier 705.

In various embodiments, the leak barrier 705 may be indented a depth 735a of 0.1, 0.2, 0.3, 0.4, 0.5, 0.6, 0.7, 0.8, 0.9, or 1.0 mm below or into a wall of the blood cartridge. In one embodiment, the leak barrier 705 has a depth 735a of 0.5 mm below or into a wall of the blood cartridge. In various embodiments, the width 730 of the leak barrier 705 may be between 0.5 and 2.5 mm. In one embodiment, the width 730 of the leak barrier 705 is 1.5 mm.

In various embodiments, the exact location of the leak barrier 705 may vary. In one embodiment, the leak barrier 705 may reside within the duct 715, thereby collecting and storing leaked blood directly in the duct 715. In other embodiments, the leak barrier 705 resides within the mixing chamber 134a-e. For example, the distance from the leak barrier 705 to the entrance 760 of the mixing chamber 134a-e (e.g., exit of the duct 715) is between 1.0 and 6.0 mm. As depicted in FIG. 7A, the leak barrier 705 is located 5.0 mm from the entrance 760. The leak barrier 705 is positioned far enough above the reagent beads 180 located in each mixing chamber 134*a-e* such that the reagent beads 180 are not activated by direct contact with blood, nor are they activated via wetting by vapors that originate from the blood fluid.

In some embodiments, the leak barrier 705 extends from the left side of the mixing chamber 134*a-e* and has a length between 2.0 mm and 10.0 mm. In one embodiment, the length of the leak barrier 705 is 5.0 mm. This ensures that undesired blood droplets that leak downward from the duct 715 are stopped or diverted by the leak barrier 705 prior to reaching the reagent beads 180 located at the bottom of the mixing chambers 134*a-e*. In other embodiments, the leak barrier 705 spans the full distance from the left side of the mixing chamber 134*a-e* to the right side of the mixing chamber 134*a-e*. Additionally, the leak barrier 705 need not be limited to a single, horizontally oriented structure as shown in FIG. 7A. For example, the leak barrier may 705 be diagonally oriented in the mixing chamber or there may be two or more leak barriers, the additional leak barriers included as safeguards to ensure that leaked blood does not escape into the mixing chamber 134*a-e*.

In a further embodiment, rather than being indented into the wall of the mixing chamber 134*a-e*, the leak barrier 705 instead extends outward from the wall of the mixing chamber 134*a-e* to form a small shelf in the chamber onto which leaked blood droplets can land to prevent premature entry into the mixing chamber 134*a-e*. When the blood is released from the measuring chamber 132*-ae*, the blood can flow over the top of and/or around the sides of the shelf to access the bottom of the mixing chamber 134*a-e*. In various embodiments, the leak barrier 705 may be elevated 785 at a height 735*b* of 0.1, 0.2, 0.3, 0.4, 0.5, 0.6, 0.7, 0.8, 0.9, or 1.0 mm above a wall of the blood cartridge. In one embodiment, the leak barrier 705 has a height 735*b* of 0.5 above a wall of the blood cartridge, as shown in FIG. 7C.

The leak barrier 705 can be created using a variety of techniques including, but not limited to overmolding, molding, photo-etching, photolithography, laser engraving, or 3-dimenstional printing. As one example, the leak barrier 705 may be molded on the wall of the right cover 126 through the pouring of a polymer onto a first mask to form the right cover 126. As another example, the leak barrier 705 may be overmolded in the main body 124. A polymer is poured into a first mask, which includes the inverse of the shape of the leak barrier (e.g. a protrusion). The polymer forms the hard plastic main body 124 including the leak barrier 705 in each mixing chamber 134*a-e*.

Returning to FIG. 7A, in various embodiments, a first type of reagent bead 720 is located on the left side of the mixing chamber 134*a-e* and a second type of reagent bead 725 is located on the right side of the mixing chamber 134*a-e*. As previously described, the respective beads 720 and 725 are held in their positions by the multiple retaining elements 182. In one embodiment, the orientation of the first 720 and second type of reagent beads 725 is important for conducting extrinsically activated thromboelastometry (EXTEM) or intrinsically activated thromboelastometry (INTEM) assays.

For example, for an EXTEM assay, the first type of reagent bead 720 on the left side of the chamber may be a heparin neutralizing agent (e.g. polybrene), a platelet blocking agent (e.g. cytochalasin D), an antifibrinolytic agent (e.g. tranexamic acid or aprotinin), or a combination of these. These reagents must be dissolved first upon exposure to blood. The second type of reagent bead 725 located on the right side of the chamber include the activator (e.g. tissue factor) or recalcifier (e.g. $CaCl_2$)) reagents. Therefore, when blood is allowed to enter from the measuring chamber 132*a-e* to the mixing chamber 134*a-e*, the blood enters from the duct 715 located on the left side of the mixing chamber 134*a-e* and the first type of reagent bead 720, e.g. polybrene, would be exposed to the blood prior to the second type of reagent bead 725, e.g. $CaCl_2$). Blood passes over the leak barrier 705, which helps to guide the blood along the left side of the mixing chamber to specific dissolvable reagent beads (e.g. the first type of reagent bead 720) which is located directly below the leak barrier 705.

FIG. 7D depicts an alternative embodiment of the mixing chamber 134*a-e* with a leak barrier 705 and a blood guide 710 that directs the flow of blood within the mixing chamber 134*a-e*. Further reference will be made in regards to FIG. 7E, which shows a side view, termed Section B-B, of the blood guide 710 that extends outward from the wall 750 of the right cover 126. Section B-B depicts the blood guide 710 from a top-to-bottom manner, as indicated by the dotted arrows in FIG. 7D.

In various embodiments, the blood guide 710 is molded on a wall of the right cover 126. Referring to FIG. 7E, the blood guide 710 is an elongated ridge that extends outward from a wall 750 of the right cover 126 and contacts a wall 775 of the mixing chamber 134*a-e*. In various embodiments, the surface 740 of the blood guide 710 is sealed with the wall 775 of the mixing chamber 134*a-e* to prevent blood from traversing the blood guide 710. In other embodiments, the blood guide 710 is located on a wall of the mixing chamber 134*a-e* and is an elongated ridge that extends outward from the wall of the mixing chamber 134*a-e*. In some embodiments, the blood guide 710 may be an indentation in a wall of the blood cartridge as opposed to an elevated elongated ridge.

In various embodiments, the surface 740 of the blood guide 710 may not be sealed with an opposing wall. Thus, the blood guide has a height between 0.5 and 1.5 mm. For example, the blood guide 710 may have a height of 1.0 mm. In various embodiments, the blood guide 710 is indented 0.5 mm below the wall of the blood cartridge device. In various embodiments, the blood guide 710 has a width between 0.5 and 2.5 mm. For example, the blood guide 710 has a width of 1.5 mm.

The combination of a leak barrier 705 and blood guide 710 may be employed in situations where the blood entering the mixing chamber 134*a-e* is diluted. Diluted blood has significantly lower viscosity and may therefore rapidly distribute throughout the mixing chamber 134*a-e*. To prevent dilute blood from reaching the second type of reagent beads 725 prematurely, this embodiment employs a blood guide 710 that extends from a top side of the mixing chamber 134*a-e* at a position that is adjacent to the duct 715. In one embodiment, the blood guide 710 extends to and terminates at the retaining element 182 located at the top left position of the array of retaining elements 182. Therefore, when the vents 166*a-e* are opened to allow for blood flow into the mixing chamber 134*a-e*, the blood passes over the leak barrier 705 and is guided by the blood guide 710 to the left side of the mixing chamber 134*a-e* to first dissolve the reagent beads 720 (e.g. polybrene) located on the left side of the mixing chamber 134*a-e*. Once the blood flows below the blood guide 710, the blood is allowed to flow to the right side of the mixing chamber 134*a-e* and dissolves the second type of reagent bead 725 (e.g. $CaCl_2$)) located on the right side of the mixing chamber 134*a-e*.

In some embodiments, the reagent beads 725 located on the right side of the mixing chamber 134a-e are held by the retaining elements 182 above a threshold height. Therefore, the vent 166a-e may be opened to allow blood flow into the mixing chamber 134a-e to dissolve the reagent beads 720 located on the left side. The vents 166a-e may be closed to temporarily stop the blood flow before the blood is able to reach the threshold height to dissolve the reagent beads located on the right side of the mixing chamber 134a-e. After a certain amount of time elapses, the vent 166a-e can be opened to continue blood flow into the mixing chamber 134a-e to dissolve the reagent beads located on the right side of the mixing chamber 134a-e.

Although FIG. 7D depicts the blood guide 710 as oriented vertically, one skilled in the art may envision alternative orientations that achieve the goal of directing blood flow to the left side of the chamber. As one example, the blood guide 710 may extend downward from a top right side of the mixing chamber 134a-e. The blood guide 710 originates from a position above the retaining elements 182 and the dissolvable reagent beads 180 and extends to the top left retaining element 182 in the array of retaining elements 182. Therefore, any blood that enters the mixing chamber 134a-e above a threshold height is redirected to towards the left side of the chamber. Other varying embodiments of the blood guide 710 may also be envisioned.

In various embodiments, the blood guide 710 may be created using a variety of techniques including, but not limited to over-molding, molding photo-etching, photolithography, laser engraving, or 3-dimenstional printing. For example, the blood guide 710 may be molded on the right cover 126. In another example, the blood guide may be overmolded in the mixing chamber 134a-e of the main body 124. A polymer is poured into a first mask, which includes the inverse of the shape of the blood guide 710. The polymer forms the hard plastic main body 124 including the blood guide 710 in each mixing chamber 134a-e.

In alternative embodiments, as illustrated in FIG. 7F, the mixing chamber 134a-e may incorporate the use of two or more blood guides 710 that directs the blood flow to a right side of the mixing chamber 134a-e. Additionally, this embodiment may be constructed without the leak barrier 705 illustrated in FIGS. 7A and 7D. In various embodiments, the one or more blood guides 710 serve as tracks that can direct the flow of blood to any part of the mixing chamber 134a-e. Therefore, specific dissolvable reagent beads 180 that need to be exposed to blood first may be located in the mixing chamber at any position such that the two or more blood guides 710 direct the blood flow first to the specific dissolvable reagent beads 180.

In FIG. 8, a left side view of cartridge 120 and individual channels 130a-e is provided. In this view there is visibility of testing chamber inlet ports 136ai, 136bi, 136ci, 136di, and 136ei for testing chambers 136a-e respectively. The inlet ports 136ai-ei are located near the top of the testing chambers 136a-e, for example, along a side wall of the chamber 136a-e. This configuration can be advantageous if the blood contains gaseous bubbles, because such gas may be allowed to escape from the blood as the blood enters the cups 136a-e. In viscous solutions, bubbles may be retained at the bottom of the cup 136a-e if the solution enters through the bottom, adversely impacting thromboelastometric measurements in the cup 136a-e. In addition, this configuration may advantageously minimize fluid flow turbulence as the blood flows into the testing chambers 136a-e.

In the depicted embodiment of FIG. 8, the cartridge 120 includes two locator pin receptacles 140a and 140b. The locator pin receptacles 140a and 140b are used to mate with locator pins of the analyzer console 140 (as described further below). In this manner, the cartridge 120 can be accurately positioned in relation to the analyzer console 140.

The cartridge 120 also includes a vacuum application port 162. When a source of vacuum is applied at the vacuum application port 162, and when the vents and valves of the cartridge 120 are in the proper configuration, blood can be drawn into the measuring chambers 132a-e as described above, and as described further below.

The cartridge 120 also includes a pressure application port 164. When a source of pressure is applied at the pressure application port 164, and when the vents and valves of the cartridge 120 are in the proper configuration, blood can be forced to flow from the measuring chambers 132a-e into the mixing chambers 134a-e, and subsequently from the mixing chambers 134a-e into the testing chambers 136a-e as described above, and as described further below.

In the depicted embodiment, the cartridge 120 also includes vents 166a, 166b, 166c, 166d, and 166e. Other cartridge embodiments may include fewer or more vents. The vents 166a-e are confluent with the mixing chambers 134a-e respectively. Accordingly, when the vents 166a-e are open to allow airflow, air from the mixing chambers 134a-e can be readily displaced from the mixing chambers 134a-e as blood flows into the mixing chambers 134a-e. Conversely, when the vents 166a-e are closed to prevent airflow, blood is inhibited from flowing into the mixing chambers 134a-e because the air within the mixing chambers 134a-e is not allowed to be displaced therefrom. The vents 166a-e can be individually opened and closed by the analyzer console 140 in accordance with predefined schemes as described further below. Accordingly, blood flow into the mixing chambers 134a-e can be controlled as desired.

In the depicted embodiment, the cartridge 120 also includes valves 168, 170, 160a, 160b, 160c, 160d, and 160e. Other cartridge embodiments may include fewer or more valves. The valves 168, 170, and 160a-e are located within fluid flow paths of the cartridge 120. Accordingly, the valves 168, 170, and 160a-e can be actuated (opened or closed) by the analyzer console 140 to allow or to prevent fluid flow through the fluid flow paths in which the valves 168, 170, and 160a-e are respectively located. For example, the valve 168 is located in the fluid flow path between the needle 123a and the measuring chamber 132a. Accordingly, when the valve 168 is open blood can flow from the needle 123a to the measuring chamber 132a, and when the valve 168 is closed blood cannot flow from the needle 123a to the measuring chamber 132a.

The valve 170 is located in the fluid flow path between the measuring chamber 132e and the overflow chamber 139. Accordingly, when the valve 170 is open blood can flow from the measuring chamber 132e to the overflow chamber 139, and when the valve 170 is closed blood cannot flow from the measuring chamber 132e to the overflow chamber 139.

The valves 160a-e are located in the fluid flow paths between the mixing chambers 134a-e and the testing chambers 136a-e respectively. Accordingly, when the valves 160a-e are open blood can flow from the mixing chambers 134a-e to the testing chambers 136a-e respectively, and when the valves 160a-e are closed blood cannot flow from the mixing chambers 134a-e to the testing chambers 136a-e.

In some embodiments the valves 160a-e can be individually actuated by pins that are translated towards and away from the valves 160a-e. To close the valves 160a-e, the pins can engage with and distend elastomer members of the valves 160a-e so that the elastomer member makes contact with a valve seat of the valves 160a-e. When such pins are retracted away from the elastomer members of the valves 160a-e, the elastomer members will rebound such that the elastomer member is no longer distended and then the valve is opened. The pins can be translated by solenoids in some embodiments.

Referring now to FIGS. 9A-9D which schematically depicts an example fluidic control process 200 that can be used with the thromboelastometry systems provided herein. The process 200 begins with blood contained only within the blood collection tube 10, and ends with blood/reagent mixtures contained in cups 136a-e that are configured for rotary thromboelastometry. It should be understood that, in some embodiments, the cartridge 120 (refer to FIGS. 1-7) that is used to implement the fluidic control process 200 is heated (e.g., to about 37° C.) prior to having any blood therein.

Figure 9A:
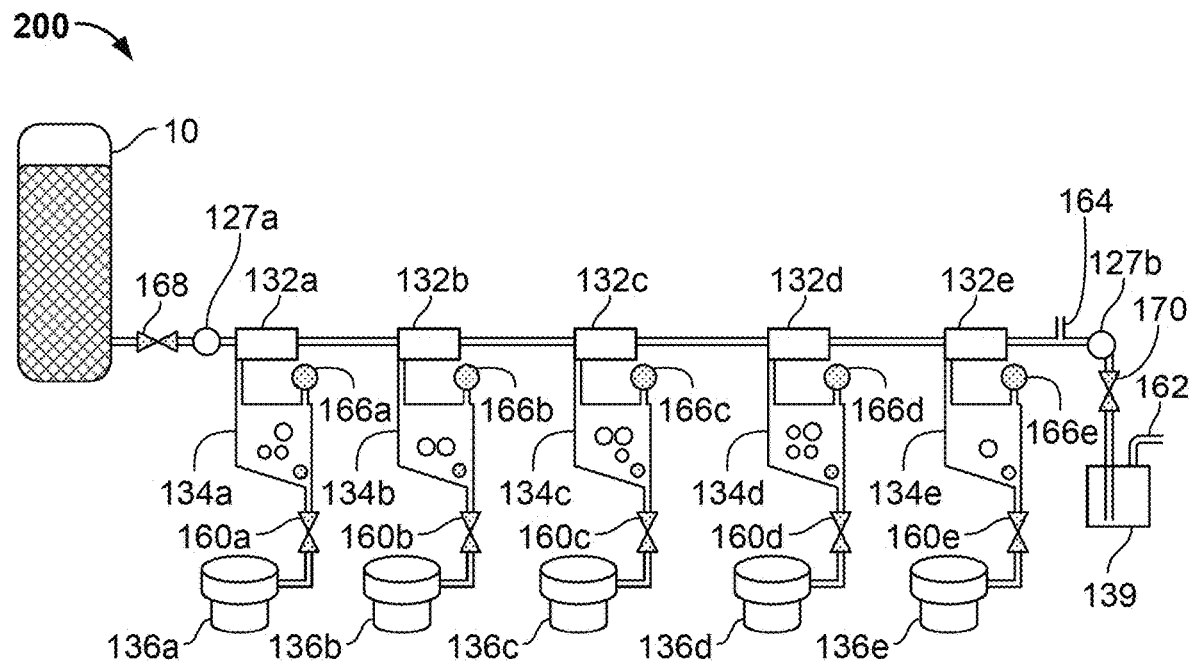
FIG. 9A-9D are a series of schematic diagrams depicting operations of the thromboelastometry system of FIGS. 1A, 1B, 2, and 3, in accordance with some embodiments.

Referring to FIG. 9A, the example fluidic control process 200 includes the blood collection tube 10, the measuring chambers 132a-e, the mixing chambers 134a-e, and cups 136a-e, the overflow chamber 139, the blood detection locations 127a and 127b, the vacuum application port 162, the pressure application port 164, the vents 166a-e, the valves 168, 170, and 160a-e. In the depicted configuration, valve 168 is closed, thereby retaining the blood substantially within the blood collection tube 10.

Figure 9B:
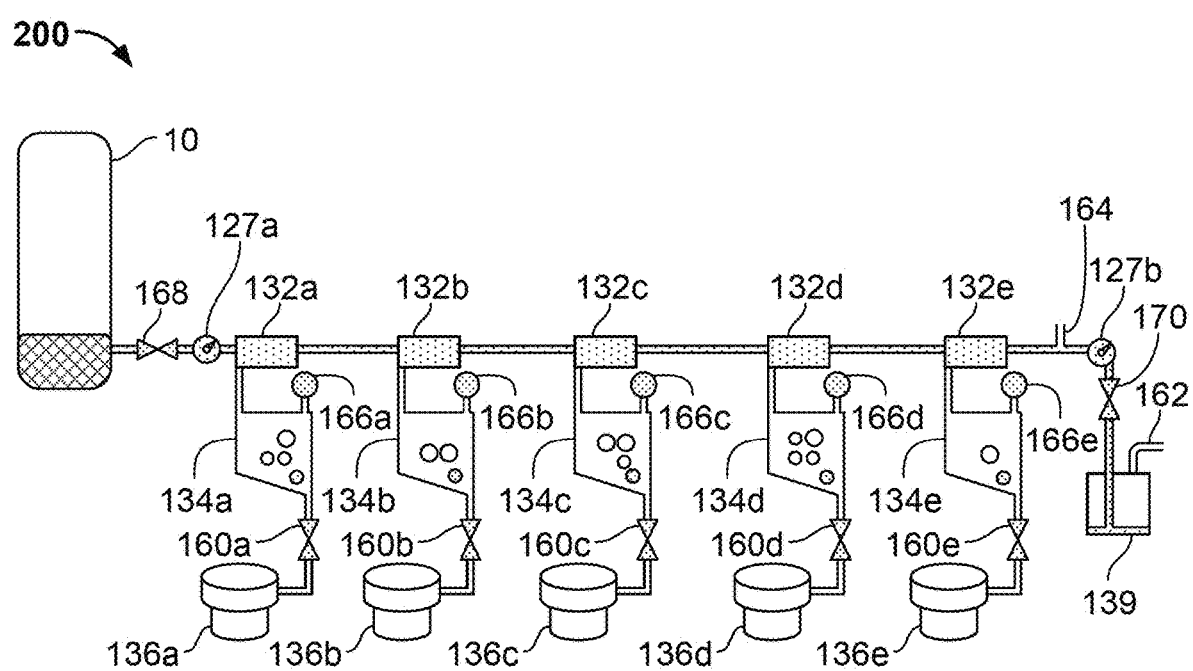

While the example fluidic control process 200 includes five blood flow channels (each comprising a measuring chamber 132a-e, a mixing chamber 134a-e, and a cup 136a-e respectively), it should be understood that having five blood flow channels is not required in all embodiments. For example, in some embodiments only a single blood flow channel is included. Alternately, two blood flow channels are included, or three blood flow channels are included, or four blood flow channels are included, or six blood flow channels are included, or more than six blood flow channels are included. Referring to FIG. 9B, the measuring chambers 132a-e are filled with blood, and a small amount of blood is contained within the overflow chamber 139. To arrive at this state, the following changes were made (in comparison to FIG. 8A) and/or the following conditions existed: (i) the valves 168 and 170 were opened, (ii) the valves 160a-e were closed, (iii) the vents 166a-e were closed, (iv) a negative pressure was applied to the vacuum application port 162, and (v) the pressure application port 164 was unpressurized. Accordingly, the blood flowed: (i) out of the blood collection tube 10, (ii) through the valve 168, (iii) through the blood detection location 127a, (iv) into and filling the measuring chamber 132a, (v) into and filling the measuring chamber 132b, (vi) into and filling the measuring chamber 132c, (vii) into and filling the measuring chamber 132d, (viii) into and filling the measuring chamber 132e, (ix) through blood detection location 127b, (x) through valve 170, and (xi) into the overflow chamber 139. When blood was detected in the blood detection location 127b, the application of the negative pressure was discontinued—thereby stopping further blood flow.

In some embodiments, the example fluidic control process 200 includes an leak barrier 705 (not shown) between one, some, or each of the measuring chambers 132a-e and the mixing chambers 134a-e. The leak barrier 705 provides a mechanism to stop blood leakage without a connection to an external control device. The application of negative pressure by opening the respective vent 166a-e creates a pressure differential on the mixing chamber side, thereby overcoming the leak barrier 705 through the sheer volume of blood flow.

In some embodiments, the example fluidic control process 200 includes a stop valve in lieu of or in addition to the leak barrier 705 between one, some, or each of the measuring chambers 132a-e and the mixing chambers 134a-e. In some embodiments, the stop valve is a snap acting valve, snapping open upon reaching a set pressure, or a modulating valve that opens in proportion to the pressure differential. Other cartridge embodiments may include pressure-controlled valves in other fluid paths.

In some embodiments, the stop valve may be opened and closed by the same mechanism provided by the valves shown in the reaction system 168, 162, 160a-e at FIGS. 8A-8H. In some embodiments, the stop valves may be opened and closed through a mechanism other than pressure application to the blood. In some embodiments, the stop valve is opened upon remote command from a control device connected to the stop valve. In some embodiments, the stop valve can be actuated by the analyzer console 140 to allow or to prevent fluid flow through the fluid path from the measuring chamber 132a-e to the mixing chamber 134a-e.

Figure 9C:
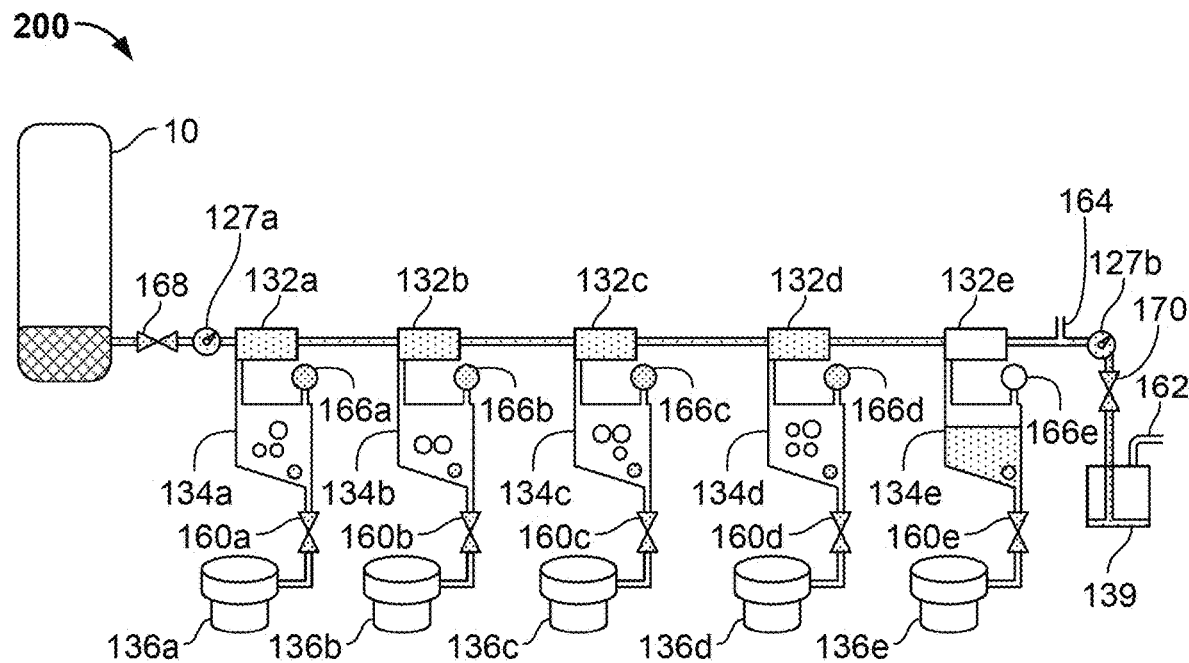

Referring to FIG. 9C, the measuring chambers 132a-d are still filled with blood, but the blood from the measuring chamber 132e has transferred to the mixing chamber 134e. To arrive at this state, the following changes were made (in comparison to FIG. 9B) and/or the following conditions existed: (i) the valves 168 and 170 were closed, (ii) the valves 160a-e remained closed, (iii) the vents 166a-d remained closed, (iv) the vent 166e was opened, and (v) a source of air pressure was applied to the pressure application port 164. Accordingly, the blood flowed: (i) out of the measuring chamber 132e, and (ii) into the mixing chamber 134e. Because the vents 166a-d and the valves 160a-d remained closed, the blood in the measuring chambers 132a-d did not flow into the mixing chambers 134a-d. In some embodiments, the fluidic control process 200 shown in FIG. 9C includes blood guides 710 (not shown) located in the mixing chamber 134e that directs the flow of blood within the mixing chamber 134e. With blood in the mixing chamber 134e, the mixing element in mixing chamber 134e can move and agitate the blood to facilitate the dissolving of the reagent beads therein.

Figure 9D:
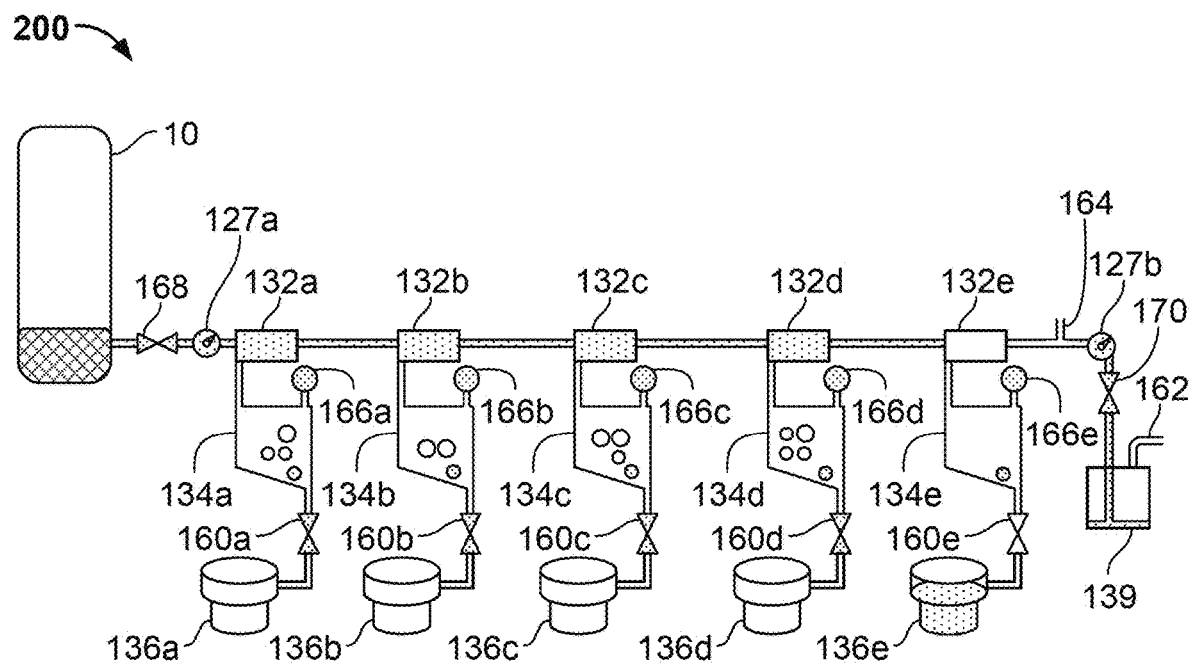

Referring to FIG. 9D, the measuring chambers 132a-d are still filled with blood, and the blood/reagent mixture that was in the mixing chamber 134e (refer to FIG. 9C) has transferred to the cup 136e. To arrive at this state, the following changes were made (in comparison to FIG. 9C) and/or the following conditions existed: (i) the valves 168 and 170 remained closed, (ii) the valve 160e was opened, (iii) the valves 160a-d remained closed, (iv) the vent 166e was closed (v) the vents 166a-d remained closed, and (vi) a source of air pressure was applied to the pressure application port 164. Accordingly, the blood/reagent mixture flowed: (i) out of the mixing chamber 134e, and (ii) into the cup 136e. Because the vents 166a-d and the valves 160a-d remained closed, the blood did not flow from the measuring chambers 132a-d towards the mixing chambers 134a-d. With the blood/reagent mixture located in the cup 136e, rotary thromboelastometry can begin in the cup 136e.

The process recited for filling cup 136e can be repeated for cups 136a-d. Once completed, the cups 136a-e each contains blood/reagent mixtures and rotary thromboelastometry can occur using the samples in the cups 136a-e. Performing rotary thromboelastometry is further described in application Ser. No. 14/958,876, filed on Dec. 3, 2015 which is hereby incorporated by reference in its entirety.

Throughout this specification, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, as used herein any reference to "one embodiment" or "an embodiment" or "various embodiments" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skilled in the art will appreciate still additional alternative structural and functional designs for smart frames as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A cartridge device comprising:
a measuring chamber having an inlet port located near a top of the measuring chamber and an outlet port located at a bottom of the measuring chamber;
a reagent chamber downstream from the measuring chamber, the reagent chamber comprising an entrance and an exit and one or more walls that extend from the entrance to the exit, the one or more walls forming the reagent chamber, the entrance being downstream from the outlet port, the reagent chamber being in fluid communication with the measuring chamber through the outlet port and the entrance, the reagent chamber containing one or more reagent beads that are dissolvable in blood to affect coagulation; and
a guide connected to a wall of the reagent chamber and to the entrance to the reagent chamber, at least part of the guide being inside the one or more walls forming the reagent chamber and extending part-way between the entrance and the exit, the guide being configured to receive a test sample comprising blood via the entrance and extending downward from the entrance toward a location within the reagent chamber to transport the test sample within the guide to at least one of the one or more reagent beads in the reagent chamber.

2. The cartridge device of claim 1, wherein the guide is formed using one of overmolding, molding, photo-etching, photolithography, laser engraving, or 3D printing.

3. The cartridge device of claim 1, wherein an entirety of the guide is different from the wall.

4. The cartridge device of claim 1, wherein the guide has a minimum width of 0.5 mm.

5. The cartridge device of claim 1, wherein the one or more reagent beads are retained in position in the chamber, and wherein the guide is configured to direct the test sample to a first type of the one or more reagent beads.

6. The cartridge device of claim 5, wherein the first type of the one or more reagent beads comprises one or more reagents of calcium chloride, polybrene, heparinase, cytochalasin D, tranexamic acid, tissue factor, or phospholipids.

7. The cartridge device of claim 1, wherein the guide is configured to direct the test sample to a first type of the one or more reagent beads located on one side of the reagent chamber, the first type of the one or more reagent beads comprising one or more reagents of polybrene, cytochalasin D, tranexamic acid, or aprotinin.

8. The cartridge device of claim 1, wherein the guide comprises an elongated ridge extending outward from the wall.

9. The cartridge device of claim 1, wherein the guide comprises an indentation in the wall.

10. The cartridge device of claim 1, wherein the reagent chamber comprises a mixing element, and wherein the mixing element is disposed in a bottom portion of the reagent chamber.

11. The cartridge device of claim 10, wherein the reagent chamber comprises more than one retaining elements, and wherein the retaining elements are between the one or more reagent beads and the mixing element.

12. The cartridge device of claim 1, further comprising a testing chamber downstream from, and in fluid communication, with the reagent chamber.

13. The cartridge device of claim 1, comprising:
a plurality of measuring chambers including the measuring chamber, each respective measuring chamber having an inlet port located near a top thereof and an outlet port located at a bottom thereof;
a plurality of reagent chambers including the reagent chamber, each respective reagent chamber being downstream from a corresponding measuring chamber, each respective reagent chamber comprising an entrance downstream from a corresponding measuring chamber outlet port, each respective reagent chamber being in fluid communication with the corresponding measuring chamber through a respective outlet port and a respective entrance, and each respective reagent chamber containing one or more reagent beads that are dissolvable in blood; and
a plurality of guides including the guide, each respective guide being within a corresponding reagent chamber and being configured to transport a respective test sample comprising blood within the guide to the one or more reagent beads within the corresponding reagent chamber.

14. The cartridge device of claim 13, wherein the one or more reagent beads in each respective reagent chamber comprises one or more reagents of calcium chloride, polybrene, heparinase, cytochalasin D, tranexamic acid, tissue factor, or phospholipids.

15. The cartridge device of claim 13, wherein the one or more reagent beads in each respective reagent chamber are retained in position in each respective reagent chamber.

16. The cartridge device of claim 15, wherein the plurality of guides are each configured to direct a test sample to a first type of the one or more reagent beads in each respective reagent chamber.

17. The cartridge device of claim 13, wherein the plurality of guides each comprises an elongated ridge extending outward from a wall of a corresponding reagent chamber.

18. The cartridge device of claim 13, wherein each of the reagent chambers comprises a mixing element, and wherein each respective mixing element is disposed in a bottom portion of a corresponding reagent chamber.

19. The cartridge device of claim 13, wherein each of the reagent chambers comprises more than one retaining elements, and wherein each respective retaining element is between one or more reagent beads and a corresponding mixing element.

20. The cartridge device of claim 13, further comprising a plurality of testing chambers, each respective testing chamber being in fluid communication, with a corresponding reagent chamber.

* * * * *